United States Patent
Jung et al.

(10) Patent No.: US 12,037,337 B2
(45) Date of Patent: Jul. 16, 2024

(54) COMPOUND AND ORGANIC LIGHT EMITTING DEVICE COMPRISING THE SAME

(71) Applicant: LG CHEM, LTD., Seoul (KR)

(72) Inventors: Min Woo Jung, Daejeon (KR); Dong Hoon Lee, Daejeon (KR); Boon Jae Jang, Daejeon (KR); Wanpyo Hong, Daejeon (KR); Sang Duk Suh, Daejeon (KR); Jungha Lee, Daejeon (KR); Su Jin Han, Daejeon (KR); Seulchan Park, Daejeon (KR); Sunghyun Hwang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 657 days.

(21) Appl. No.: 17/281,335

(22) PCT Filed: Nov. 22, 2019

(86) PCT No.: PCT/KR2019/016161
§ 371 (c)(1),
(2) Date: Mar. 30, 2021

(87) PCT Pub. No.: WO2020/111673
PCT Pub. Date: Jun. 4, 2020

(65) Prior Publication Data
US 2021/0399232 A1 Dec. 23, 2021

(30) Foreign Application Priority Data

Nov. 27, 2018 (KR) .................... 10-2018-0148563
Nov. 21, 2019 (KR) .................... 10-2019-0150702

(51) Int. Cl.
*H01L 51/00* (2006.01)
*C07D 403/14* (2006.01)
(Continued)

(52) U.S. Cl.
CPC .......... *C07D 487/04* (2013.01); *C07D 403/14* (2013.01); *C07D 405/14* (2013.01);
(Continued)

(58) Field of Classification Search
CPC ............ H01L 51/0072; H01L 51/0067; H01L 51/0052; H01L 51/5016; H01L 51/0074;
(Continued)

(56) References Cited

U.S. PATENT DOCUMENTS 9,577,199 B2    2/2017  Lecloux et al.
2004/0251816 A1  12/2004  Leo et al.
(Continued)

FOREIGN PATENT DOCUMENTS

CN    101087776 A    12/2007
CN    100366703      2/2008
(Continued)

OTHER PUBLICATIONS

Lee, D. R. et al., "Bis(diphenyltriazine) as a new acceptor of efficient thermally activated delayed flourescent emitters," Dyes and Pigments (2018), doi: 10.1016/j.dyepig.2017.12.048, 32 pages.
(Continued)

*Primary Examiner* — Robert D Harlan
(74) *Attorney, Agent, or Firm* — Bryan Cave Leighton Paisner LLP

(57) ABSTRACT

Provided is compound of Chemical Formula 1:

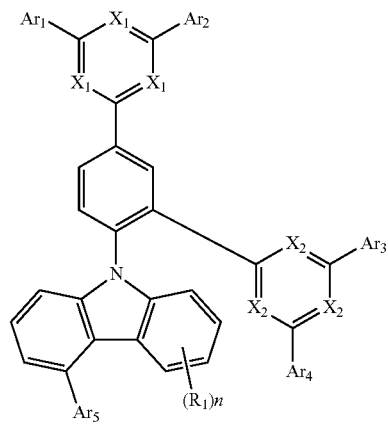

wherein:
each $X_1$ is independently N or CH, provided that at least one of them is N;
each $X_2$ is independently N or CH, provided that at least one of them is N;
$Ar_1$ to $Ar_4$ are each independently a substituted or unsubstituted $C_{6-60}$ aryl or a substituted or unsubstituted $C_{5-60}$ heteroaryl containing one or more of N, O, and S;
$Ar_5$ is a substituted or unsubstituted $C_{6-60}$ aryl or a substituted or unsubstituted $C_{5-60}$ heteroaryl containing one or more of N, O, and S;
each $R_1$ is independently hydrogen, deuterium, a substituted or unsubstituted $C_{1-60}$ alkyl, a substituted or unsubstituted $C_{3-60}$ cycloalkyl, a substituted or unsubstituted $C_{6-60}$ aryl, or a substituted or unsubstituted $C_{5-60}$ heteroaryl containing one or more of N, O, and S; and
n is an integer of 0 to 4,
and an organic light emitting device including the same.

10 Claims, 2 Drawing Sheets

(51) Int. Cl.

| | | |
|---|---|---|
| *C07D 405/14* | (2006.01) | |
| *C07D 409/14* | (2006.01) | |
| *C07D 487/04* | (2006.01) | |
| *C07D 487/14* | (2006.01) | |
| *C07D 491/048* | (2006.01) | |
| *C07D 493/22* | (2006.01) | |
| *C07D 495/04* | (2006.01) | |
| *C07D 495/22* | (2006.01) | |
| *C07D 519/00* | (2006.01) | |
| *C09K 11/06* | (2006.01) | |
| *H10K 85/60* | (2023.01) | |
| *H10K 50/11* | (2023.01) | |
| *H10K 101/00* | (2023.01) | |
| *H10K 101/10* | (2023.01) | |
| *H10K 101/40* | (2023.01) | |

(52) U.S. Cl.
CPC ........ *C07D 409/14* (2013.01); *C07D 487/14* (2013.01); *C07D 491/048* (2013.01); *C07D 493/22* (2013.01); *C07D 495/04* (2013.01); *C07D 495/22* (2013.01); *C07D 519/00* (2013.01); *C09K 11/06* (2013.01); *H10K 85/615* (2023.02); *H10K 85/622* (2023.02); *H10K 85/626* (2023.02); *H10K 85/654* (2023.02); *H10K 85/656* (2023.02); *H10K 85/6572* (2023.02); *H10K 85/6574* (2023.02); *H10K 85/6576* (2023.02); *C09K 2211/1018* (2013.01); *H10K 50/11* (2023.02); *H10K 2101/10* (2023.02); *H10K 2101/40* (2023.02); *H10K 2101/90* (2023.02)

(58) Field of Classification Search
CPC . H01L 51/0058; C07D 403/14; C07D 405/14; C07D 409/14; C09K 11/06
See application file for complete search history.

(56) References Cited

U.S. PATENT DOCUMENTS

| | | | |
|---|---|---|---|
| 2009/0191426 | A2 | 7/2009 | Yabe et al. |
| 2010/0187505 | A1 | 7/2010 | Stoessel et al. |
| 2012/0126221 | A1 | 5/2012 | Kitamura et al. |
| 2012/0126692 | A1 | 5/2012 | Ise et al. |
| 2012/0205640 | A1 | 8/2012 | Kai et al. |
| 2013/0240796 | A1 | 9/2013 | Parham et al. |
| 2013/0292654 | A1 | 11/2013 | Matsunaga et al. |
| 2014/0114069 | A1 | 4/2014 | Kim et al. |
| 2015/0218191 | A1 | 8/2015 | Sannomiya et al. |
| 2015/0380662 | A1 | 12/2015 | Kim et al. |
| 2016/0329502 | A1 | 11/2016 | Dyatkin et al. |
| 2017/0047522 | A1 | 2/2017 | Noda et al. |
| 2017/0117488 | A1 | 4/2017 | Ahn et al. |
| 2017/0244043 | A1 | 8/2017 | Kim et al. |
| 2018/0123049 | A1 | 5/2018 | Lee et al. |
| 2018/0145262 | A1 | 5/2018 | Zeng et al. |
| 2018/0170914 | A1 | 6/2018 | Miyata et al. |
| 2018/0248127 | A1 | 8/2018 | Lee et al. |
| 2019/0019960 | A1 | 1/2019 | Zink et al. |
| 2019/0237680 | A1 | 8/2019 | Kim et al. |
| 2019/0288222 | A1* | 9/2019 | Moon ................ C07D 401/14 |
| 2020/0044163 | A1 | 2/2020 | Hung et al. |
| 2020/0115364 | A1 | 4/2020 | Aguilera-Iparraguirre et al. |
| 2020/0331898 | A1 | 10/2020 | Seifermann |
| 2022/0271233 | A1 | 8/2022 | Yoon et al. |

FOREIGN PATENT DOCUMENTS

| | | |
|---|---|---|
| CN | 103764786 | 4/2014 |
| CN | 107667102 | 2/2018 |
| CN | 107880028 | 4/2018 |
| CN | 107935914 | 4/2018 |
| CN | 107954922 | 4/2018 |
| CN | 107987009 | 5/2018 |
| CN | 109251199 A | 1/2019 |
| CN | 112533900 A | 3/2021 |
| DE | 102016112377 | 1/2018 |
| JP | 2009-155300 A | 7/2009 |
| JP | 2009-158848 A | 7/2009 |
| JP | 2010-030937 | 2/2010 |
| JP | 4474493 | 6/2010 |
| JP | 4590020 | 12/2010 |
| JP | 4729642 | 7/2011 |
| JP | 2014-141571 | 8/2014 |
| JP | 2018-035129 | 3/2018 |
| KR | 10-2000-0051826 | 8/2000 |
| KR | 10-2010-0131939 | 12/2010 |
| KR | 10-2012-0018231 | 2/2012 |
| KR | 10-2012-0033711 | 4/2012 |
| KR | 10-2012-0098694 | 9/2012 |
| KR | 10-2012-0109744 | 10/2012 |
| KR | 10-2013-0020398 | 2/2013 |
| KR | 10-2013-0130236 | 12/2013 |
| KR | 10-2014-0014959 | 2/2014 |
| KR | 10-2014-0015240 | 2/2014 |
| KR | 10-1396171 | 5/2014 |
| KR | 10-2014-0139307 | 12/2014 |
| KR | 10-2015-0061174 | 6/2015 |
| KR | 10-2015-0063462 | 6/2015 |
| KR | 10-2015-0105201 | 9/2015 |
| KR | 10-2015-0129282 A | 11/2015 |
| KR | 10-2015-0139459 | 12/2015 |
| KR | 10-2016-0003362 | 1/2016 |
| KR | 10-2016-0041768 | 4/2016 |
| KR | 10-2016-0066339 | 6/2016 |
| KR | 10-2016-0129190 | 11/2016 |
| KR | 10-2017-0049291 | 5/2017 |
| KR | 10-2017-0060836 | 6/2017 |
| KR | 10-2017-0076292 A | 7/2017 |
| KR | 10-2017-0079348 | 7/2017 |
| KR | 10-2017-0097820 | 8/2017 |
| KR | 10-2017-0113808 | 10/2017 |
| KR | 10-2017-0116993 | 10/2017 |
| KR | 10-2018-0027468 | 3/2018 |
| KR | 10-2018-0047306 | 5/2018 |
| KR | 10-2018-0063708 | 6/2018 |
| KR | 10-2018-0065276 | 6/2018 |
| KR | 10-2018-0092035 | 8/2018 |
| KR | 10-2018-0098809 | 9/2018 |
| KR | 10-2018-0109747 | 10/2018 |
| KR | 10-1926771 | 12/2018 |
| KR | 10-2019-0008129 | 1/2019 |
| KR | 10-2019-0108094 | 9/2019 |
| KR | 10-2020-0047418 | 5/2020 |
| KR | 10-2020-0063053 | 6/2020 |
| TW | 2019-12640 | 4/2019 |
| WO | 2003-012890 A2 | 2/2003 |
| WO | 2003-012890 A3 | 8/2003 |
| WO | 2012-005362 | 1/2012 |
| WO | 2013-027906 | 2/2013 |
| WO | 2016-089080 | 6/2016 |
| WO | 2016-181846 | 11/2016 |
| WO | 2017-190885 | 11/2017 |
| WO | 2018/147638 A1 | 8/2018 |
| WO | 2018/237385 A1 | 12/2018 |
| WO | 2019-076844 | 4/2019 |
| WO | 2019/086297 A1 | 5/2019 |
| WO | 2019121112 | 6/2019 |

OTHER PUBLICATIONS

Park, H. et al., "A directly coupled dual emitting core based molecular design of thermally activated delayed fluorescent emitters," J. Mater. Chem. C., 5:12143-12150 (2017).

Chan Seok Oh et al., "Dihedral Angle Control of Blue Thermally Activated Delayed Fluorescent Emitters through Donor Substitution Position for Efficient Reverse Intersystem Crossing", ACS Appl. Mater. Interfaces 10: 35420-35429 (2018).

Kang et al., "High-efficiency blue organic light-emitting Diodes using emissive carbazole-triazine-based donor-acceptor molecules

(56) References Cited

OTHER PUBLICATIONS with high reverse intersystem crossing rates," Organic Electronics 75 (2019): 105399, 7 pages (2019).
Braveenth et al., "Triazine-Acceptor-Based Green Thermally Activated Delayed Fluorescence Materials for Organic Light-Emitting Diodes," Materials 2019, 12, 2646, 19 pages (2019).
International Search Report and the Written Opinion of PCT/KR2019/016161, mailed Mar. 9, 2020.
U.S. Appl. No. 17/278,406.
U.S. Appl. No. 17/278,757.
U.S. Appl. No. 17/275,664.
Office Action of Korean Patent Office in Appl'n No. 10-2019-0142729 dated May 24, 2021.
Office Action of Korean Patent Office in Appl'n No. 10-2019-0140736 dated May 24, 2021.
Notice of Allowance of Korean Patent Office in Appl'n No. 10-2019-0145261 dated May 26, 2021.
Office Action of Korean Patent Office in Appl'n No. 10-2019-0142730 dated May 26, 2021.
Office Action of Korean Patent Office in Appl'n No. 10-2019-0150702 dated May 31, 2021.

\* cited by examiner

[FIG. 1]
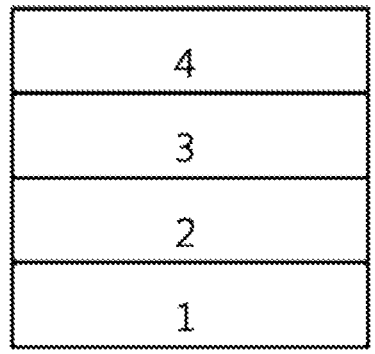
[FIG. 2]
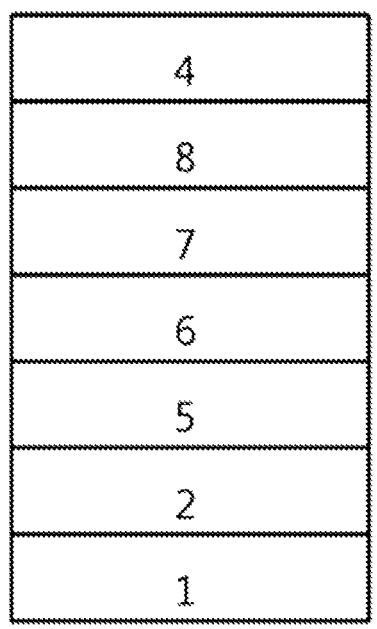

[FIG. 3]

| |
|---|
| 4 |
| 10 |
| 8 |
| 7 |
| 9 |
| 6 |
| 5 |
| 2 |
| 1 |

COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2019/016161 filed on Nov. 22, 2019, which claims priority to or the benefit of Korean Patent Application No. 10-2018-0148563 filed with the Korean Intellectual Property Office on Nov. 27, 2018, and Korean Patent Application No. 10-2019-0150702 filed with the Korean Intellectual Property Office on Nov. 21, 2019, the disclosures of which are incorporated herein by reference in their entirety.

TECHNICAL FIELD

The present disclosure relates to a novel compound and an organic light emitting device including the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

PRIOR ART LITERATURE

Patent Literature (Patent Literature 1) Korean Unexamined Patent Publication No. 10-2000-0051826

BRIEF DESCRIPTION

Technical Problem

It is an object of the present disclosure to provide a novel compound and an organic light emitting device including the same.

Technical Solution

One aspect of the present disclosure provides a compound of Chemical Formula 1:

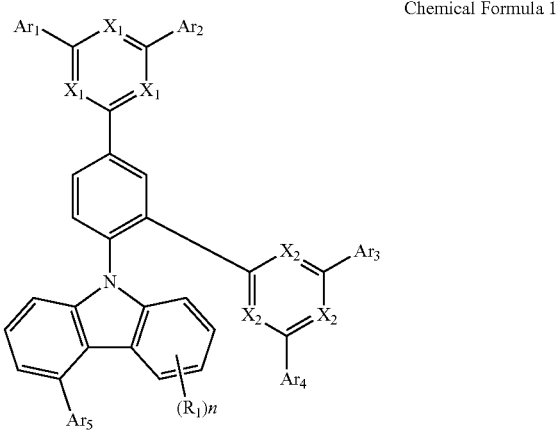

Chemical Formula 1 wherein, in Chemical Formula 1:
each $X_1$ is independently N or CH, with the proviso that at least one of them is N;
each $X_2$ is independently N or CH, with the proviso that at least one of them is N;
$Ar_1$ to $Ar_4$ are each independently a substituted or unsubstituted $C_{6-60}$ aryl or a substituted or unsubstituted $C_{5-60}$ heteroaryl containing any one or more heteroatoms selected from the group consisting of N, O, and S;
$Ar_5$ is a substituted or unsubstituted $C_{6-60}$ aryl or a substituted or unsubstituted $C_{5-60}$ heteroaryl containing any one or more heteroatoms selected from the group consisting of N, O, and S;
each $R_1$ is independently hydrogen, deuterium, a substituted or unsubstituted $C_{1-60}$ alkyl, a substituted or unsubstituted $C_{3-60}$ cycloalkyl, a substituted or unsubstituted $C_{6-60}$ aryl, or a substituted or unsubstituted $C_{5-60}$ heteroaryl containing one or more heteroatoms selected from the group consisting of N, O, and S; and
n is an integer of 0 to 4.

Another aspect of the present disclosure provides an organic light emitting device including a first electrode; a second electrode that is disposed opposite to the first electrode; and one or more organic material layers that are disposed between the first electrode and the second electrode, wherein one or more layers of the organic material layers include the compound of Chemical Formula 1.

Advantageous Effects

The compound of Chemical Formula 1 described above can be used as a material of an organic material layer of an organic light emitting device and can improve the efficiency, achieve low driving voltage and/or improve lifetime characteristics in the organic light emitting device. In particular, the compound of Chemical Formula 1 can be used as a hole injection material, hole transport material, hole injection and transport material, light emitting material, electron transport material, or electron injection material.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 7, an electron transport layer 8 and a cathode 4.

FIG. 3 shows an example of an organic light emitting device comprising a substrate 1, an anode 2, a hole injection layer 5, a hole transport layer 6, an electron blocking layer 9, a light emitting layer 7, an electron transport layer 8, an electron injection layer 10 and a cathode 4.

DETAILED DESCRIPTION

Hereinafter, embodiments of the present disclosure will be described in more detail to facilitate understanding of the invention.

One embodiment of the present disclosure provides a compound of Chemical Formula 1.

As used herein, the notation

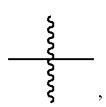

or means a bond linked to another substituent group.

As used herein, the term "substituted or unsubstituted" means being unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, or a heterocyclic group containing at least one of N, O and S atoms, or being unsubstituted or substituted with a substituent to which two or more substituents are linked among the substituents exemplified above. For example, "the substituent to which two or more substituents are linked" can be a biphenyl group. That is, the biphenyl group can also be an aryl group and can be interpreted as a substituent to which two phenyl groups are linked.

In the present specification, the number of carbon atoms of a carbonyl group is not particularly limited, but is preferably 1 to 40. Specifically, the carbonyl group can be a compound having the following structural formulae but is not limited thereto:

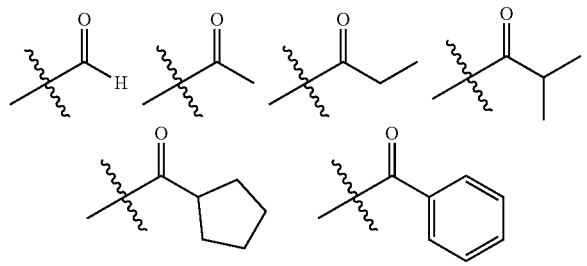

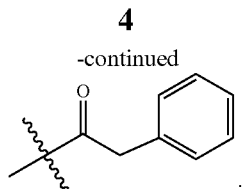

In the present specification, an ester group can have a structure in which oxygen of the ester group can be substituted by a straight-chain, branched-chain, or cyclic alkyl group having 1 to 25 carbon atoms, or an aryl group having 6 to 25 carbon atoms. Specifically, the ester group can be a compound having the following structural formulae, but is not limited thereto:

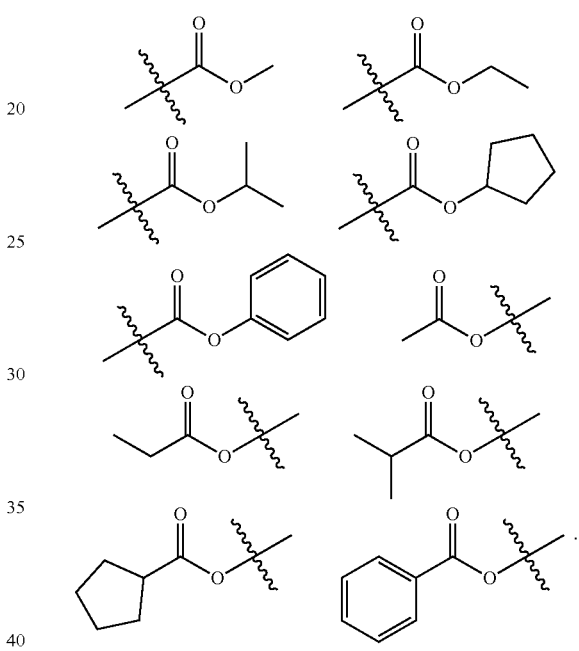

In the present specification, the number of carbon atoms of an imide group is not particularly limited, but is preferably 1 to 25. Specifically, the imide group can be a compound having the following structural formulae, but is not limited thereto:

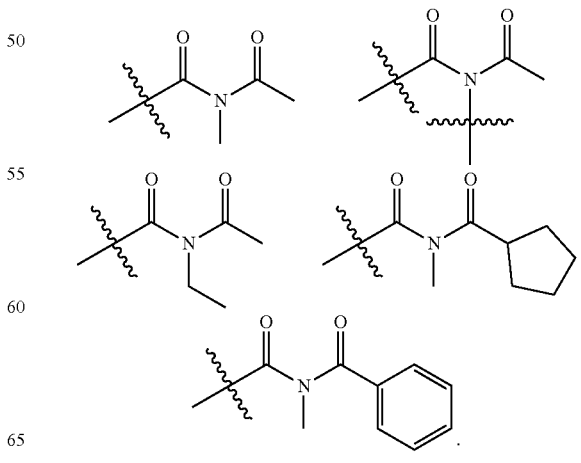

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, or iodine.

In the present specification, the alkyl group can be a straight-chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group can be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and can be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group can be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group or the like, but is not limited thereto.

In the present specification, a fluorenyl group can be substituted, and two substituent groups can be connected with each other to form a spiro structure. In the case where the fluorenyl group is substituted,

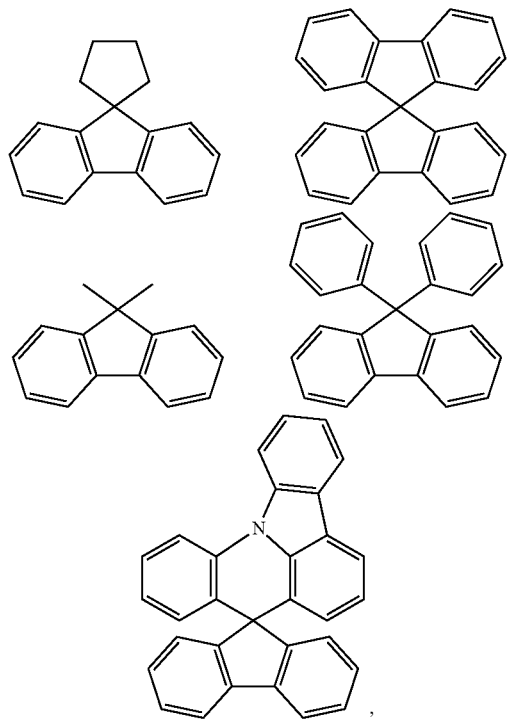

and the like can be formed. However, the structure is not limited thereto.

In the present specification, a heterocyclic group is a heterocyclic group including one or more of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, a triazol group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, a thiazolyl group, an isoxazolyl group, an oxadiazolyl group, an thiadiazolyl group, a benzothiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine can be applied to the aforementioned description of the heterocyclic group. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocycle is not a monovalent group but formed by combining two substituent groups.

Preferably, $Ar_1$ to $Ar_4$ can each independently be a phenyl, biphenyl, or naphthyl.

Preferably, all of $Ar_1$ to $Ar_4$ can be a phenyl.

Preferably, $Ar_5$ can be a phenyl, biphenyl, naphthyl, dibenzofuranyl, or dibenzothiophenyl.

Preferably, $Ar_5$ can be a phenyl.

Preferably, $X_1$ can all be N.

Preferably, $X_2$ can all be N.

Preferably, n can be 0.

For example, the compound of Chemical Formula 1 can be selected from the group consisting of the following compounds:

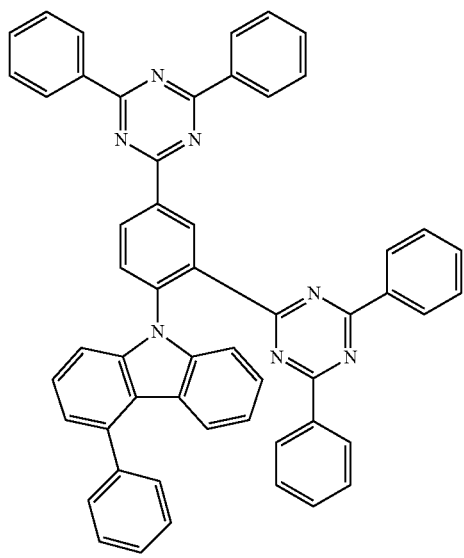

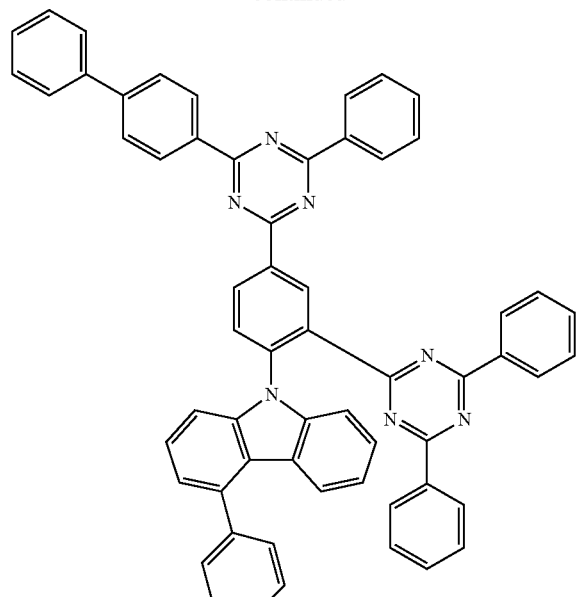

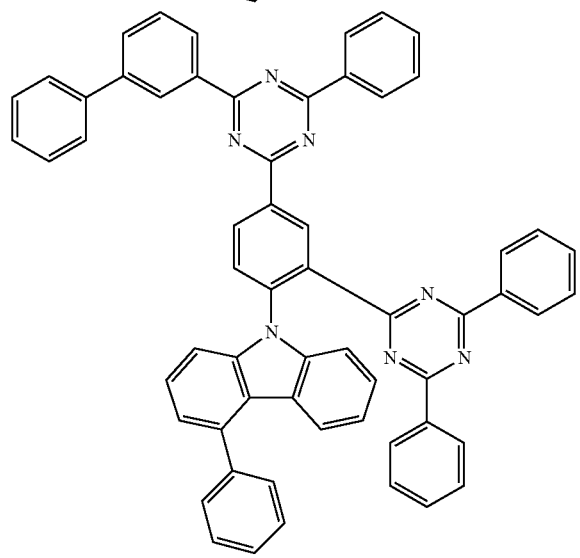

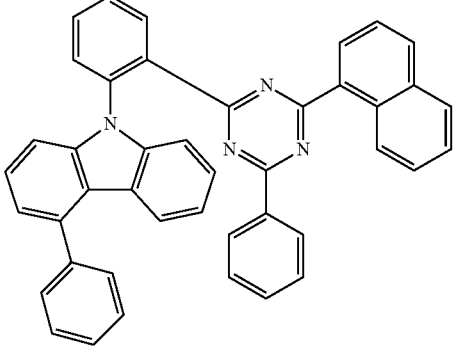

-continued
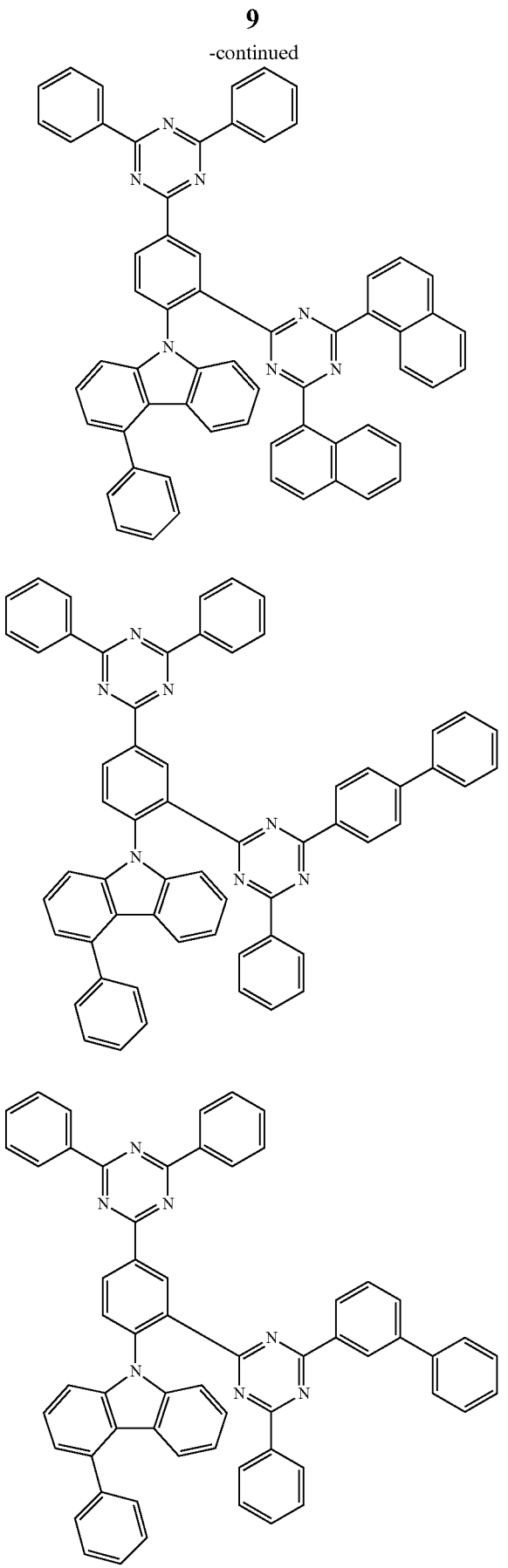
-continued
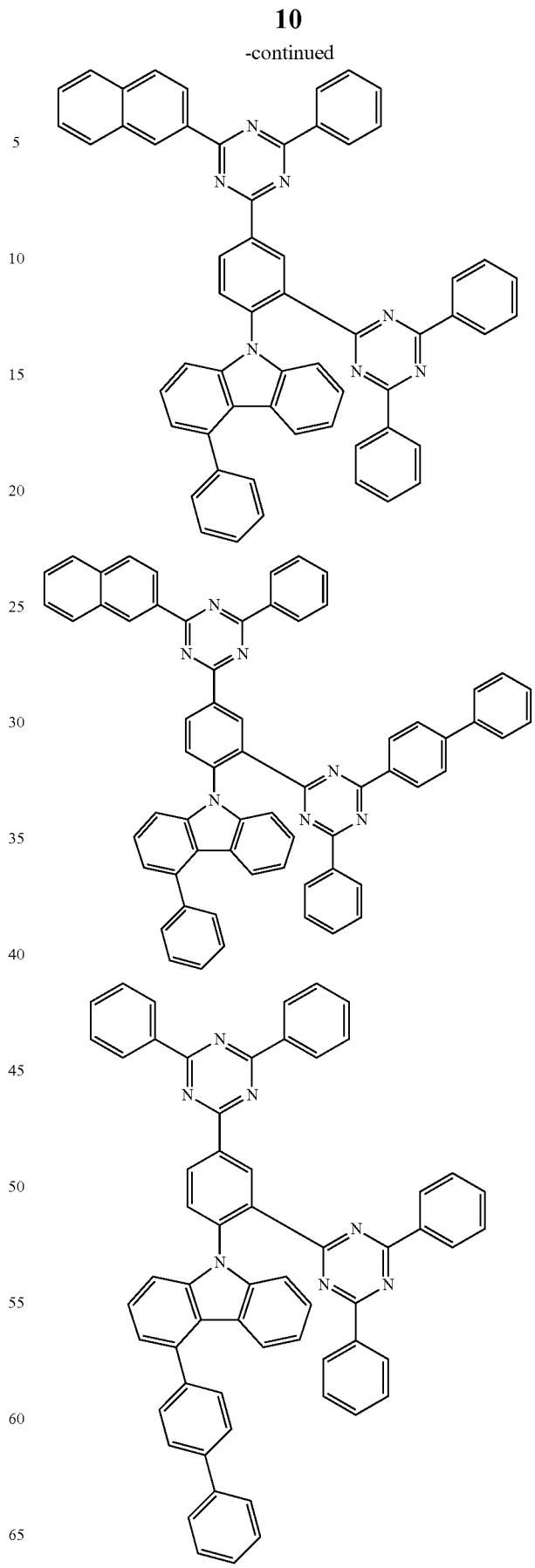

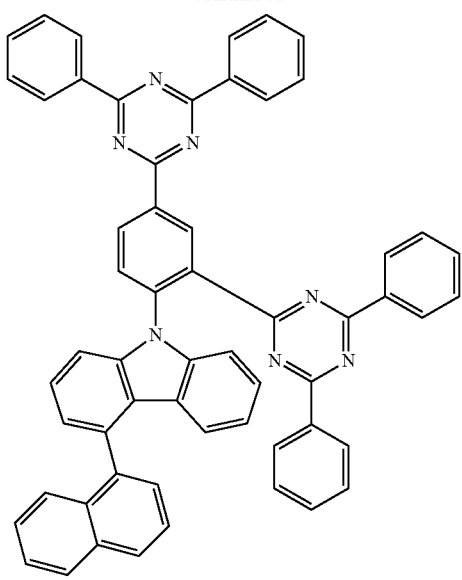
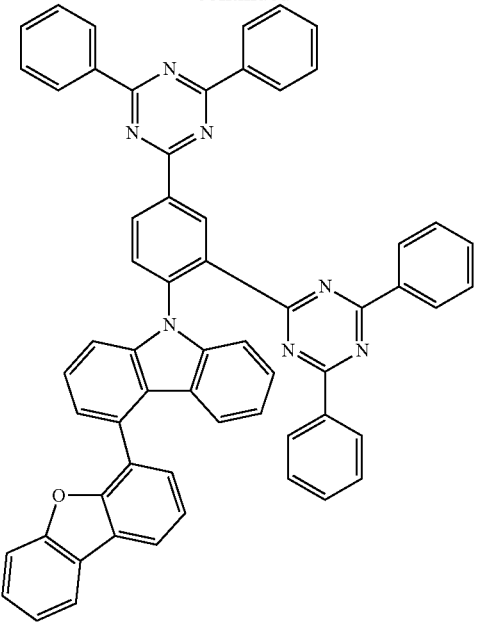
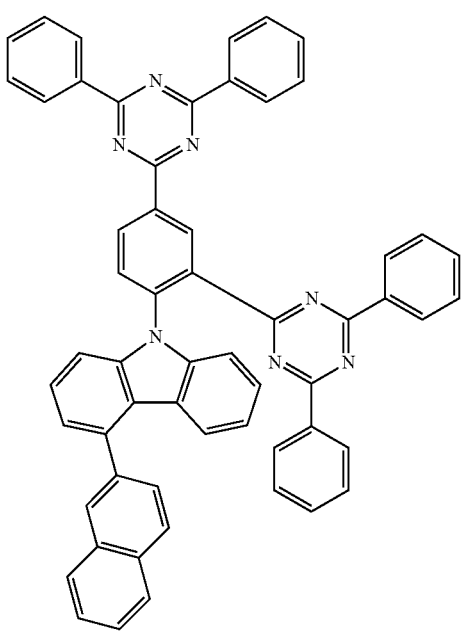
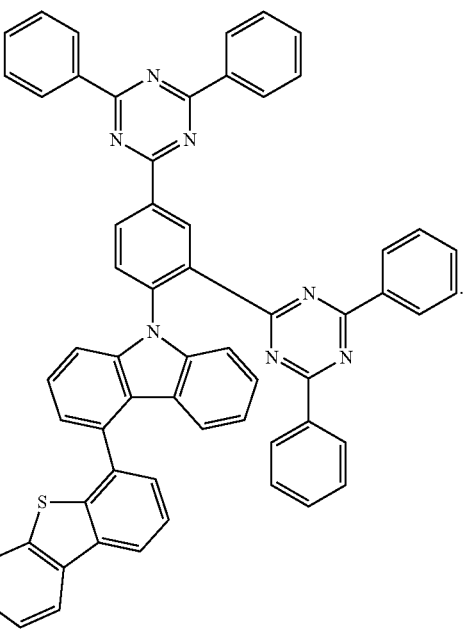
Meanwhile, the compound of Chemical Formula 1 can be prepared, for example, in accordance with a preparation method as shown in Reaction Scheme 1 below.

<Reaction Scheme 1>

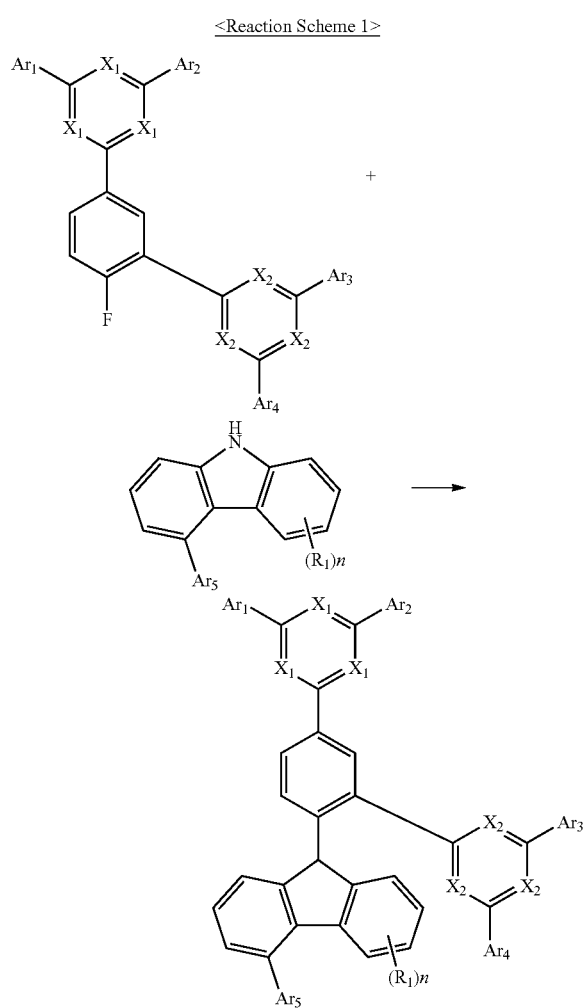

In Reaction Scheme 1, the definitions of the substituents are the same as those described above and the above preparation method can be further embodied in the Preparation Examples described hereinafter.

Another embodiment of the present disclosure provides an organic light emitting device including a compound of Chemical Formula 1 described above. As an example, there is provided an organic light emitting device including a first electrode; a second electrode that is disposed opposite to the first electrode; and one or more organic material layers that are disposed between the first electrode and the second electrode, wherein one or more layers of the organic material layers include the compound of Chemical Formula 1.

The organic material layer of the organic light emitting device of the present disclosure can have a single-layer structure, or it can have a multilayered structure in which two or more organic material layers are stacked. For example, the organic light emitting device of the present disclosure can have a structure comprising a hole injection layer, a hole transport layer, a light emitting layer, an electron transport layer, an electron injection layer and the like as the organic material layer. However, the structure of the organic light emitting device is not limited thereto, and it can include a smaller number of organic material layers.

Further, the organic material layer can include a hole injection layer, a hole transport layer, a layer for simultaneously performing hole injection and transport or an electron blocking layer, wherein the hole injection layer, the hole transport layer, the layer for simultaneously performing hole injection and transport or the electron blocking layer can include the compound of Chemical Formula 1.

Further, the organic material layer can include a light emitting layer, wherein the light emitting layer can include the compound of Chemical Formula 1. At this time, the compound of Chemical Formula 1 can be used as a host material in the light emitting layer, and more specifically, the compound of Chemical Formula 1 can be used as a host used in the light emitting layer of the green organic light emitting device.

Further, the light emitting layer can include two or more kinds of hosts, and when the light emitting layer includes two or more kinds of hosts, one or more of the hosts can be a compound of Chemical Formula 1.

Further, the organic material layer can include a hole blocking layer, an electron transport layer, an electron injection layer, or a layer for simultaneously performing electron injection and electron transport, wherein the hole blocking layer, the electron transport layer, the electron injection layer, or the layer for simultaneously performing electron injection and electron transport can include a compound of Chemical Formula 1.

Figure 3:
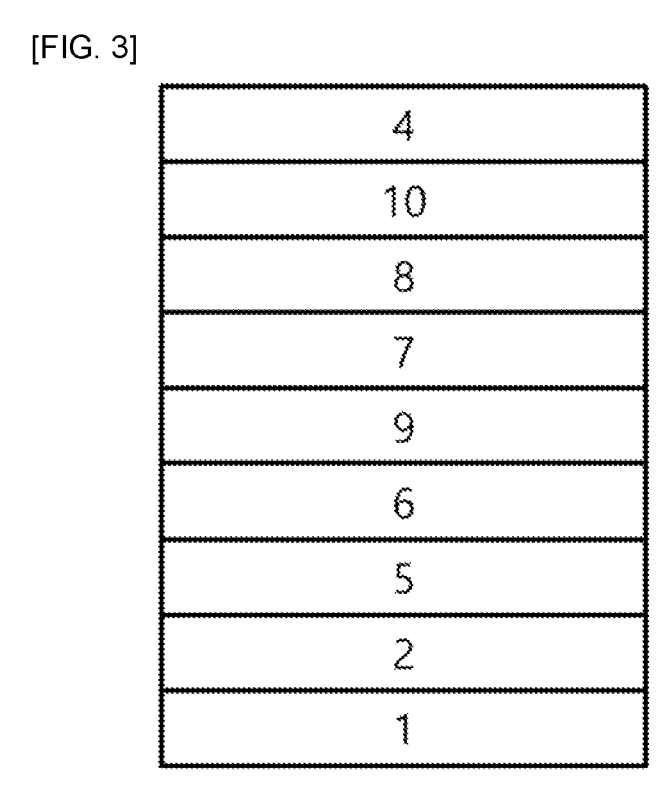

Further, the organic light emitting device according to the present disclosure can be a normal type organic light emitting device in which an anode, one or more organic material layers, and a cathode are sequentially stacked on a substrate. Further, the organic light emitting device according to the present disclosure can be an inverted type organic light emitting device in which a cathode, one or more organic material layers, and an anode are sequentially stacked on a substrate. For example, the structure of an organic light emitting device according to an embodiment of the present disclosure is illustrated in FIGS. 1 to 3.

FIG. 1 shows an example of an organic light emitting device comprising a substrate 1, an anode 2, a light emitting layer 3, and a cathode 4. In such a structure, the compound of Chemical Formula 1 can be included in the light emitting layer.

FIG. 2 shows an example of an organic light emitting device comprising a substrate 1, an anode 2, a hole injection layer 5, a hole transport layer 6, a light emitting layer 7, an electron transport layer 8 and a cathode 4. In such a structure, the compound of Chemical Formula 1 can be included in the hole injection layer, the hole transport layer, the light emitting layer and the electron transport layer.

FIG. 3 shows an example of an organic light emitting device comprising a substrate 1, an anode 2, a hole injection layer 5, a hole transport layer 6, an electron blocking layer 9, a light emitting layer 7, an electron transport layer 8, an electron injection layer 10 and a cathode 4. In such a structure, the compound of Chemical Formula 1 can be included in one or more layers of the hole injection layer, the hole transport layer, the electron blocking layer, the light emitting layer, the electron transport layer and the electron injection layer.

The organic light emitting device according to the present disclosure can be manufactured by materials and methods known in the art, except that one or more layers of the organic material layers include the compound of Chemical Formula 1. In addition, when the organic light emitting device includes a plurality of organic material layers, the organic material layers can be formed of the same material or different materials.

For example, the organic light emitting device according to the present disclosure can be manufactured by sequentially stacking a first electrode, an organic material layer and a second electrode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device can be manufactured by sequentially depositing a cathode material, an organic material layer and an anode material on a substrate.

In addition, the compound of Chemical Formula 1 can be formed into an organic material layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device can be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a hole injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer, and it is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The electron blocking layer is formed on the hole transport layer, preferably provided in contact with the light emitting layer, and severs to adjust the hole mobility, prevent excessive movement of electrons and increase the probability of hole-electron coupling, thereby improving the efficiency of the organic light emitting device. The electron blocking layer includes an electron blocking material, and as such electron blocking material, a material having a stable structure in which electrons may not flow out of the light emitting layer is suitable. Specific examples thereof can include an arylamine-based organic material or the like, but are not limited thereto.

The light emitting material is preferably a material which can receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$), a carbazole-based compound, a dimerized styryl compound, BAlq, a 10-hydroxybenzoquinoline-metal compound, a benzoxazole-based compound, a benzothiazole-based compound, a benzimidazole-based compound, a poly(p-phenylenevinylene)(PPV)-based polymer, a spiro compound, polyfluorene, rubrene, and the like, but are not limited thereto.

The light emitting layer can include a host material and a dopant material. The host material can be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The hole blocking layer is formed on the hole transport layer, and preferably, the hole blocking layer is provided in contact with the light emitting layer, and severs to prevent excessive movement of holes and increase the probability of hole-electron coupling, thereby improving the efficiency of the organic light emitting device. The hole blocking layer includes a hole blocking material, and as such hole blocking material, a material having a stable structure in which holes may not flow out of the light emitting layer is suitable. As the hole blocking material, a compound into which an electron-withdrawing group is introduced, such as azine derivatives including triazine, triazole derivatives, oxadiazole derivatives, phenanthroline derivatives, and phosphine oxide derivatives can be used, but is not limited thereto.

The electron transport layer is a layer which receives electrons from an electron injection layer and transports the electrons to a light emitting layer, and an electron transport material is suitably a material which can receive electrons effectively from a cathode and transfer the electrons to a light emitting layer, and has a large mobility for electrons. Specific examples of the electron transport material include: an Al complex of 8-hydroxyquinoline, a complex including $Alq_3$, an organic radical compound, a hydroxyflavone-metal complex, and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure can be a front side emission type, a back side emission type, or a double side emission type according to the used material.

In addition, the compound of Chemical Formula 1 can be included in an organic solar cell or an organic transistor in addition to an organic light emitting device.

The preparation of the compound of Chemical Formula 1 and the organic light emitting device containing the same will be described in detail in the following examples. However, these examples are presented for illustrative purposes only, and are not intended to limit the scope of the present disclosure.

SYNTHESIS EXAMPLE

Synthesis Example 1: Preparation of Compound 1

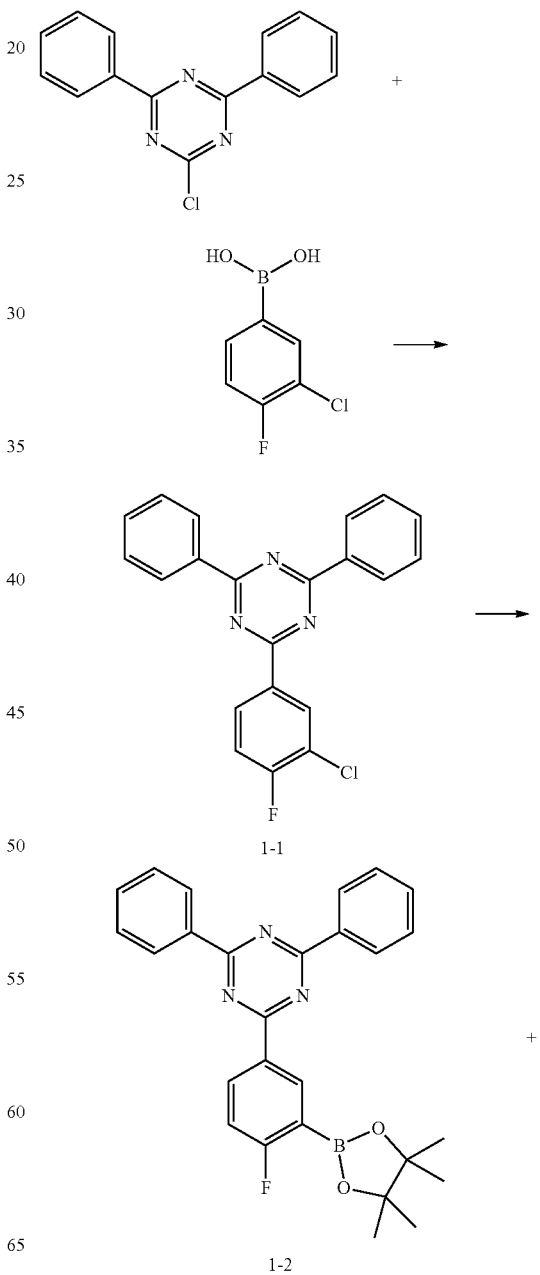

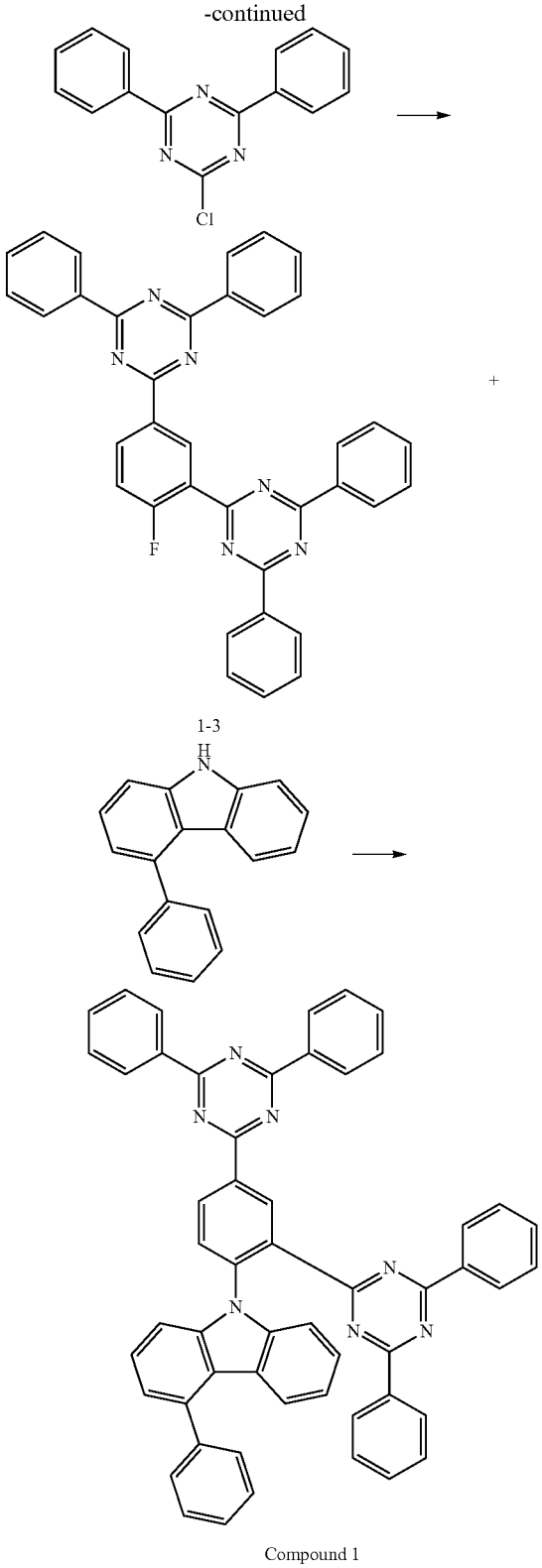

Compound 1

1) Preparation of Compound 1-1

2-Chloro-4,6-diphenyl-1,3,5-triazine (30 g, 107.2 mmol) and (3-chloro-4-fluorophenyl)boronic acid (18.6 g, 107.2 mmol) were added to 600 ml of tetrahydrofuran under a nitrogen atmosphere, and the mixture was stirred and refluxed. Then, potassium carbonate (44.4 g, 321.5 mmol) was dissolved in 44 ml of water, added thereto and sufficiently stirred, and then tetrakistriphenyl-phosphinopalladium (3.7 g, 3.2 mmol) was added. After reacting for 1 hour, the reaction mixture was cooled to room temperature, the organic layer and the aqueous layer were separated, and the organic layer was distilled. This was added again to 971 ml (20 times the amount) of chloroform, dissolved and washed twice with water. The organic layer was then separated, anhydrous magnesium sulfate was added, stirred and then filtered. The filtrate was distilled under reduced pressure. The concentrated compound was recrystallized from ethyl acetate to give a white solid compound 1-1 (27.5 g, 71%, MS: [M+H]+=362.1).

2) Preparation of Compound 1-2

Compound 1-1 (30 g, 83.1 mmol) and bis(pinacolato) diboron (21.1 g, 83.1 mmol) were added to 600 ml of dioxane under a nitrogen atmosphere, and the mixture was stirred and refluxed. Then, potassium acetate (24 g, 249.3 mmol) was added thereto and sufficiently stirred, and then palladium dibenzylidene acetone palladium (1.4 g, 2.5 mmol) and tricyclohexylphosphine (1.4 g, 5 mmol) were added. After reacting for 6 hours, the reaction mixture was cooled to room temperature and then the organic layer was subjected to filtration treatment to remove a salt, and then the filtered organic layer was distilled. This was added again to 377 ml (10 times the amount) of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethanol to give a white solid compound 1-2 (20 g, 53%, MS: [M+H]+=454.2).

3) Preparation of Compound 1-3

Compound 1-2 (20 g, 44.1 mmol) and 2-chloro-4,6-diphenyl-1,3,5-triazine (11.8 g, 44.1 mmol) were added to 400 ml of tetrahydrofuran under a nitrogen atmosphere, and the mixture was stirred and refluxed. Then, potassium carbonate (18.3 g, 132.4 mmol) was dissolved in 18 ml of water, added thereto and sufficiently stirred, and then tetrakistriphenyl-phosphinopalladium (1.5 g, 1.3 mmol) was added. After reacting for 2 hours, the reaction mixture was cooled to room temperature, the organic layer and the aqueous layer were separated, and the organic layer was distilled. This was added again to 493 ml (20 times the amount) of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethyl acetate to give a white solid compound 1-3 (15.5 g, 63%, MS: [M+H]+=559.2).

4) Preparation of Compound 1

Compound 1-3 (10 g, 17.9 mmol) and 4-phenyl-9H-carbazole (4.4 g, 17.9 mmol) were added to 200 ml of dimethylformamide under a nitrogen atmosphere, and the mixture was stirred and refluxed. Then, sodium tert-butoxide (11.4 g, 53.7 mmol) was added thereto and sufficiently stirred, and then bis(tri-tert-butylphosphine)palladium (0.3 g, 0.5 mmol) was added. After reacting for 5 hours, the reaction mixture was cooled to room temperature and then the organic layer was subjected to filtration treatment to remove a salt, and then the filtered organic layer was distilled. This was added again to 140 ml (10 times the amount) of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 1 (8.4 g, 60%, MS: [M+H]+=782.3).
Synthesis Example 2: Preparation of Compound 2
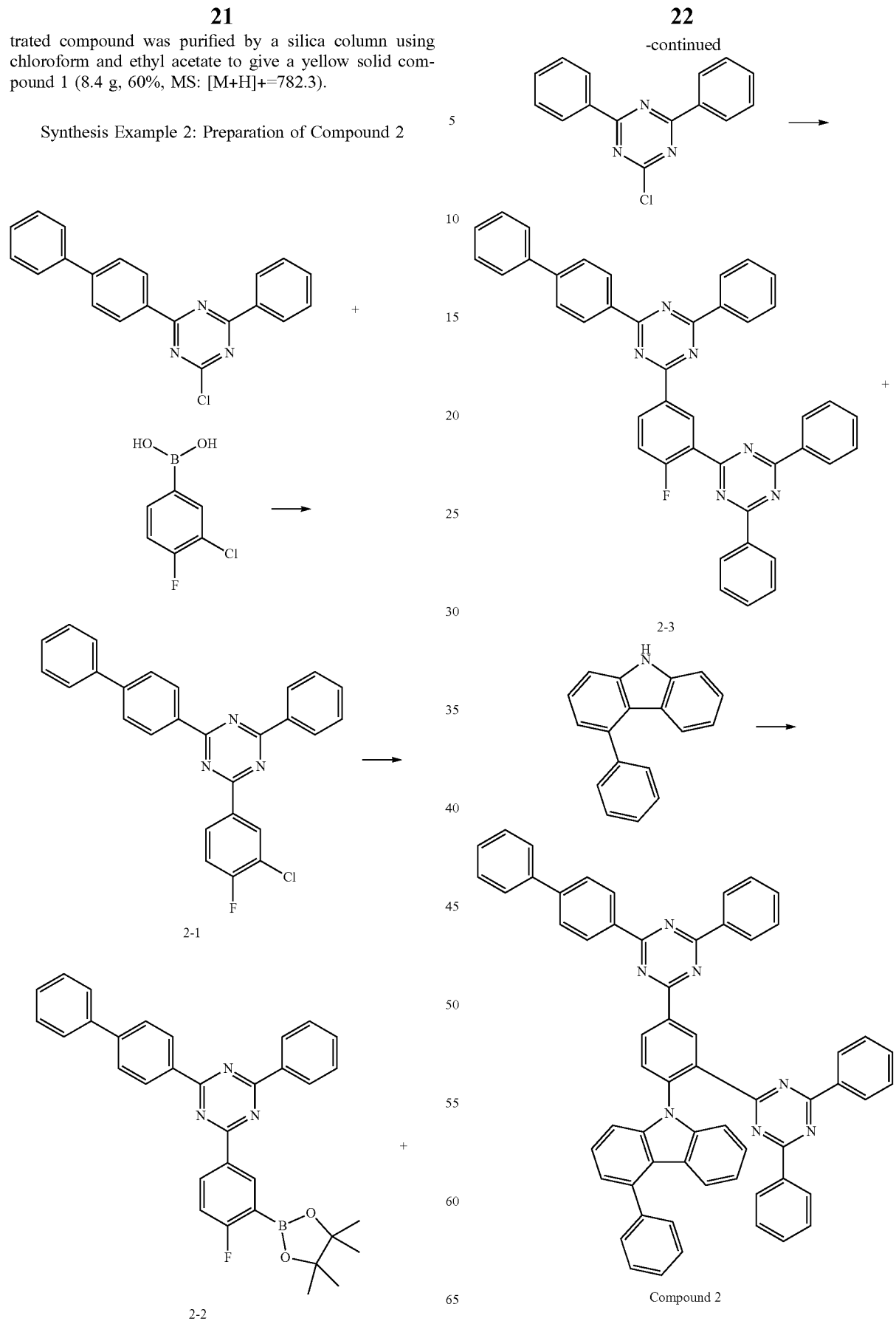

1) Preparation of Compound 2-1

2-([1,1'-biphenyl]-4-yl)-4-chloro-6-phenyl-1,3,5-triazine (30 g, 87.4 mmol) and (3-chloro-4-fluorophenyl)boronic acid (15.2 g, 87.4 mmol) were added to 600 ml of tetrahydrofuran under a nitrogen atmosphere, and the mixture was stirred and refluxed. Then, potassium carbonate (36.3 g, 262.3 mmol) was dissolved in 36 ml of water, added thereto and sufficiently stirred, and then tetrakistriphenyl-phosphinopalladium (3 g, 2.6 mmol) was added. After reacting for 2 hours, the reaction mixture was cooled to room temperature and then the produced solid was filtered. The solid was added to 764 ml (20 times the amount) of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethyl acetate to give a white solid compound 2-1 (30.2 g, 79%, MS: [M+H]+=438.1).

2) Preparation of Compound 2-2

Compound 2-1 (30 g, 68.6 mmol) and bis(pinacolato)diboron (17.4 g, 68.6 mmol) were added to 600 ml of dioxane under a nitrogen atmosphere, and the mixture was stirred and refluxed. Then, potassium acetate (19.8 g, 205.9 mmol) was added thereto and sufficiently stirred, and then palladium dibenzylidene acetone palladium (1.2 g, 2.1 mmol) and tricyclohexylphosphine (1.2 g, 4.1 mmol) were added. After reacting for 7 hours, the reaction mixture was cooled to room temperature and then the organic layer was subjected to filtration treatment to remove a salt, and then the filtered organic layer was distilled. This was added again to 363 ml (10 times the amount) of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethanol to give a white solid compound 2-2 (29.1 g, 80%, MS: [M+H]+=530.2).

3) Preparation of Compound 2-3

Compound 2-2 (20 g, 37.8 mmol) and 2-chloro-4,6-diphenyl-1,3,5-triazine (10.1 g, 37.8 mmol) were added to 400 ml of tetrahydrofuran under a nitrogen atmosphere, and the mixture was stirred and refluxed. Then, potassium carbonate (15.7 g, 113.4 mmol) was dissolved in 16 ml of water, added thereto and sufficiently stirred, and then tetrakistriphenyl-phosphinopalladium (1.3 g, 1.1 mmol) was added. After reacting for 3 hours, the reaction mixture was cooled to room temperature and then the produced solid was filtered. The solid was added to 479 ml (20 times the amount) of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethyl acetate to give a white solid compound 2-3 (17.3 g, 72%, MS: [M+H]+=635.2).

4) Preparation of Compound 2

Compound 2-3 (10 g, 15.8 mmol) and 4-phenyl-9H-carbazole (3.8 g, 15.8 mmol) were added to 200 ml of dimethylformamide under a nitrogen atmosphere, and the mixture was stirred and refluxed. Then, sodium tert-butoxide (10 g, 47.3 mmol) was added thereto and sufficiently stirred, and then bis(tri-tert-butylphosphine)palladium (0.2 g, 0.5 mmol) was added. After reacting for 5 hours, the reaction mixture was cooled to room temperature and then the organic layer was subjected to filtration treatment to remove a salt, and then the filtered organic layer was distilled. This was added again to 135 ml (10 times the amount) of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 2 (9.9 g, 73%, MS: [M+H]+=858.3).

Synthesis Example 3: Preparation of Compound 3

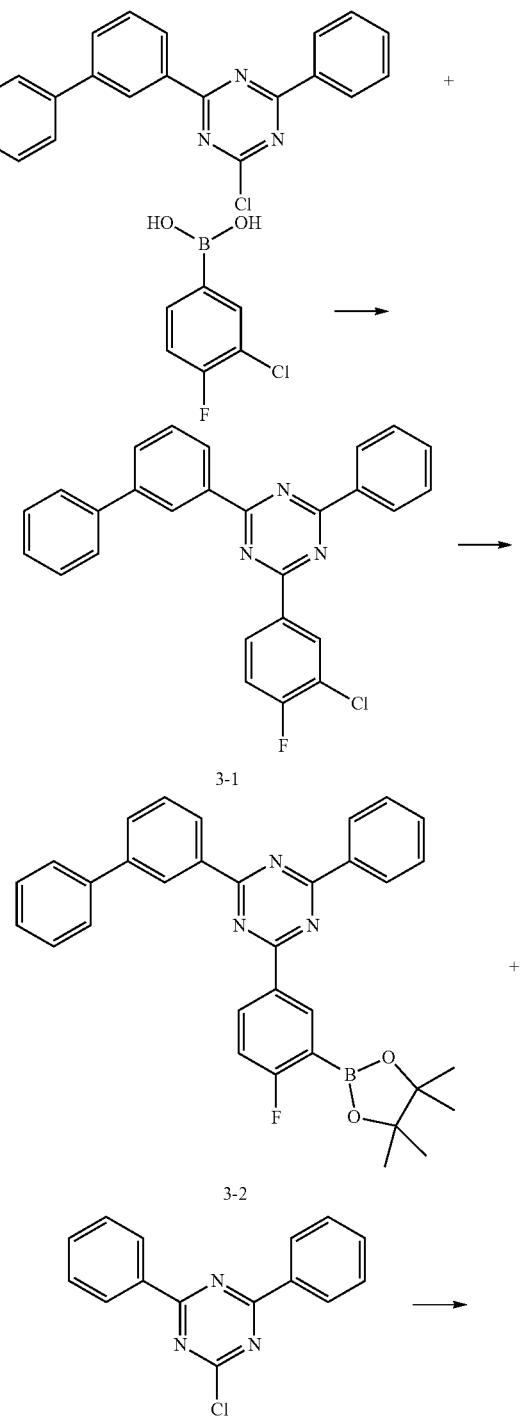

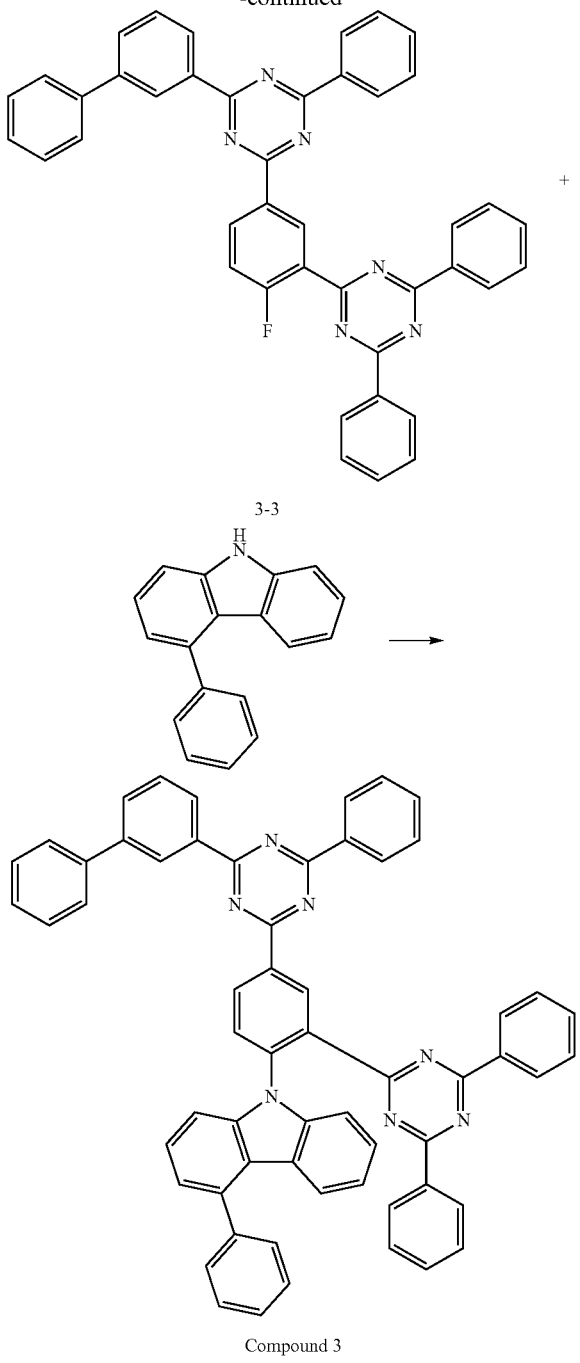

3-3

Compound 3

1) Preparation of Compound 3-1

2-([1,1'-biphenyl]-3-yl)-4-chloro-6-phenyl-1,3,5-triazine (30 g, 87.4 mmol) and (3-chloro-4-fluorophenyl)boronic acid (15.2 g, 87.4 mmol) were added to 600 ml of tetrahydrofuran under a nitrogen atmosphere, and the mixture was stirred and refluxed. Then, potassium carbonate (36.3 g, 262.3 mmol) was dissolved in 36 ml of water, added thereto and sufficiently stirred, and then tetrakistriphenyl-phosphinopalladium (3 g, 2.6 mmol) was added. After reacting for 2 hours, the reaction mixture was cooled to room temperature and then the produced solid was filtered. The solid was added to 764 ml (20 times the amount) of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethyl acetate to give a white solid compound 3-1 (22.2 g, 58%, MS: [M+H]+ =438.1).

2) Preparation of Compound 3-2

Compound 3-1 (30 g, 68.6 mmol) and bis(pinacolato) diboron (17.4 g, 68.6 mmol) were added to 600 ml of dioxane under a nitrogen atmosphere, and the mixture was stirred and refluxed. Then, potassium acetate (19.8 g, 205.9 mmol) was added thereto and sufficiently stirred, and then palladium dibenzylidene acetone palladium (1.2 g, 2.1 mmol) and tricyclohexylphosphine (1.2 g, 4.1 mmol) were added. After reacting for 6 hours, the reaction mixture was cooled to room temperature and then the organic layer was subjected to filtration treatment to remove a salt, and then the filtered organic layer was distilled. This was added again to 363 ml (10 times the amount) of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethanol to give a white solid compound 3-2 (21.1 g, 58%, MS: [M+H]+=530.2).

3) Preparation of Compound 3-3

Compound 3-2 (20 g, 37.8 mmol) and 2-chloro-4,6-diphenyl-1,3,5-triazine (10.1 g, 37.8 mmol) were added to 400 ml of tetrahydrofuran under a nitrogen atmosphere, and the mixture was stirred and refluxed. Then, potassium carbonate (15.7 g, 113.4 mmol) was dissolved in 16 ml of water, added thereto and sufficiently stirred, and then tetrakistriphenyl-phosphinopalladium (1.3 g, 1.1 mmol) was added. After reacting for 1 hour, the reaction mixture was cooled to room temperature and then the produced solid was filtered. The solid was added to 479 ml (20 times the amount) of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethyl acetate to give a white solid compound 3-3 (15.8 g, 66%, MS: [M+H]+=635.2).

4) Preparation of Compound 3

Compound 3-3 (10 g, 15.8 mmol) and 4-phenyl-9H-carbazole (3.8 g, 15.8 mmol) were added to 200 ml of dimethylformamide under a nitrogen atmosphere, and the mixture was stirred and refluxed. Then, sodium tert-butoxide (10 g, 47.3 mmol) was added thereto and sufficiently stirred, and then bis(tri-tert-butylphosphine)palladium (0.2 g, 0.5 mmol) was added. After reacting for 3 hours, the reaction mixture was cooled to room temperature and then the organic layer was subjected to filtration treatment to remove a salt, and then the filtered organic layer was distilled. This was added again to 135 ml (10 times the amount) of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 3 (8.1 g, 60%, MS: [M+H]+=858.3).

Synthesis Example 4: Preparation of Compound 4

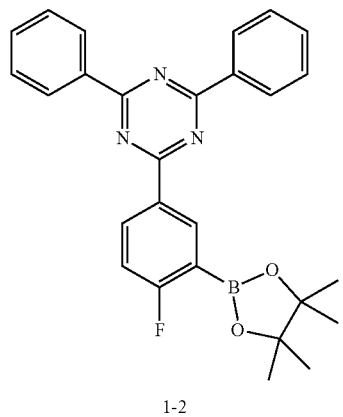

1-2

+

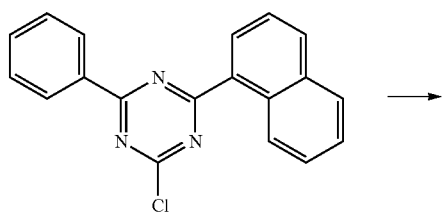

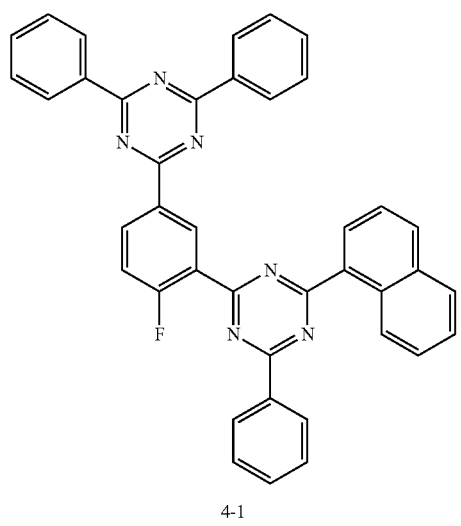

4-1

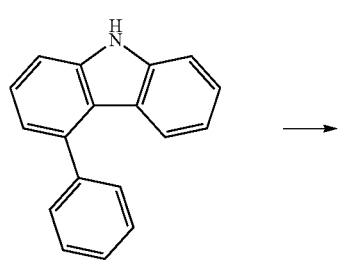

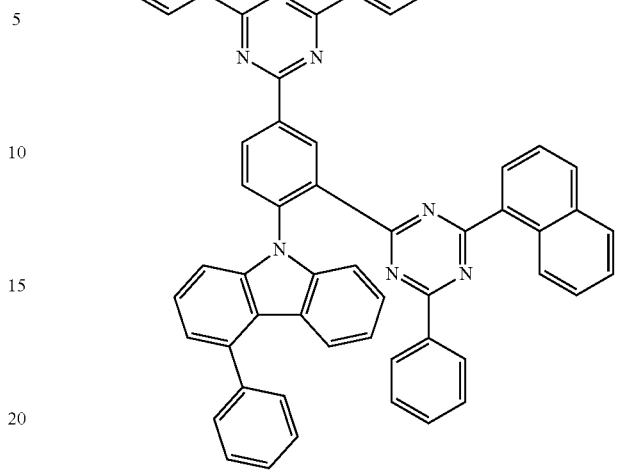

Compound 4

1) Preparation of Compound 4-1

Compound 1-2 (20 g, 44.1 mmol) and 2-chloro-4-(naphthalen-1-yl)-6-phenyl-1,3,5-triazine (14 g, 44.1 mmol) were added to 400 ml of tetrahydrofuran under a nitrogen atmosphere, and the mixture was stirred and refluxed. Then, potassium carbonate (18.3 g, 132.4 mmol) was dissolved in 18 ml of water, added thereto and sufficiently stirred, and then tetrakistriphenyl-phosphinopalladium (1.5 g, 1.3 mmol) was added. After reacting for 3 hours, the reaction mixture was cooled to room temperature and then the produced solid was filtered. The solid was added to 537 ml (20 times the amount) of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethyl acetate to give a white solid compound 4-1 (19.3 g, 72%, MS: [M+H]+=609.2).

2) Preparation of Compound 4

Compound 4-1 (10 g, 16.4 mmol) and 4-phenyl-9H-carbazole (4 g, 16.4 mmol) were added to 200 ml of dimethylformamide under a nitrogen atmosphere, and the mixture was stirred and refluxed. Then, sodium tert-butoxide (10.5 g, 49.3 mmol) was added thereto and sufficiently stirred, and then bis(tri-tert-butylphosphine)palladium (0.3 g, 0.5 mmol) was added. After reacting for 6 hours, the reaction mixture was cooled to room temperature and then the organic layer was subjected to filtration treatment to remove a salt, and then the filtered organic layer was distilled. This was added again to 141 ml (10 times the amount) of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 4 (10 g, 71%, MS: [M+H]+=858.3).

Synthesis Example 5: Preparation of Compound 5

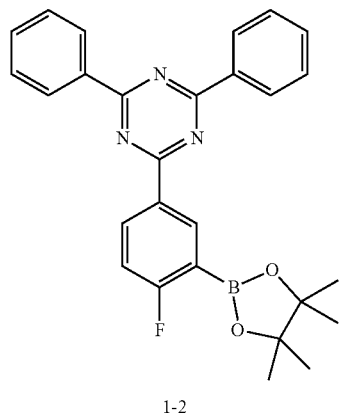

1-2

+

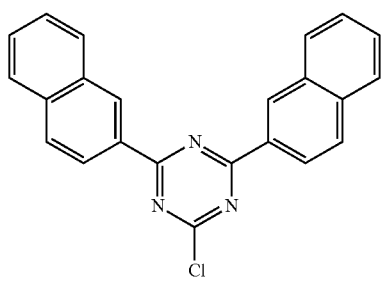

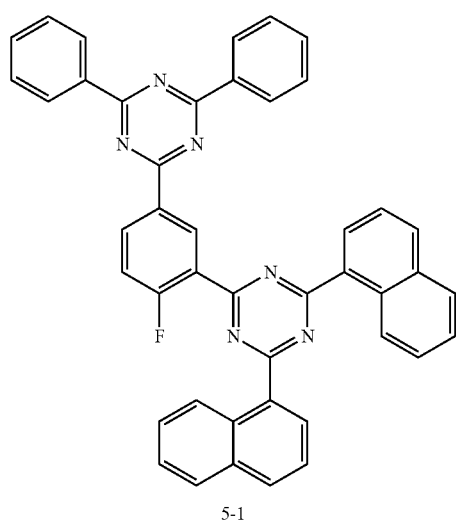

5-1

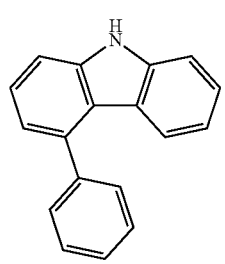

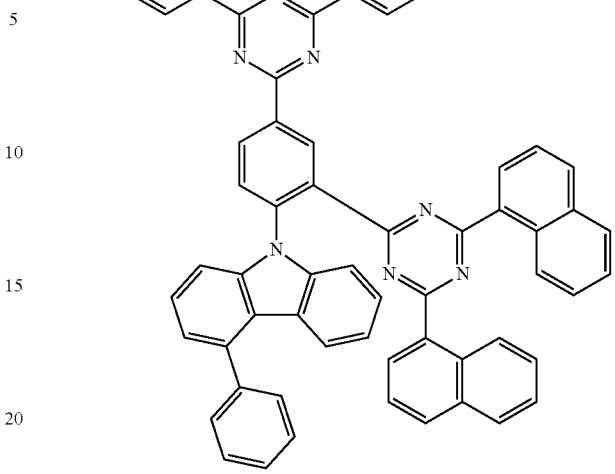

Compound 5

1) Preparation of Compound 5-1

Compound 1-2 (20 g, 44.1 mmol) and 2-chloro-4,6-di(naphthalen-2-yl)-1,3,5-triazine (16.2 g, 44.1 mmol) were added to 400 ml of tetrahydrofuran under a nitrogen atmosphere, and the mixture was stirred and refluxed. Then, potassium carbonate (18.3 g, 132.4 mmol) was dissolved in 18 ml of water, added thereto and sufficiently stirred, and then tetrakistriphenyl-phosphinopalladium (1.5 g, 1.3 mmol) was added. After reacting for 2 hours, the reaction mixture was cooled to room temperature and then the produced solid was filtered. The solid was added to 581 ml (20 times the amount) of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethyl acetate to give a white solid compound 5-1 (18.9 g, 65%, MS: [M+H]+=659.2).

2) Preparation of Compound 5

Compound 5-1 (10 g, 15.2 mmol) and 4-phenyl-9H-carbazole (3.7 g, 15.2 mmol) were added to 200 ml of dimethylformamide under a nitrogen atmosphere, and the mixture was stirred and refluxed. Then, sodium tert-butoxide (9.7 g, 45.6 mmol) was added thereto and sufficiently stirred, and then bis(tri-tert-butylphosphine)palladium (0.2 g, 0.5 mmol) was added. After reacting for 7 hours, the reaction mixture was cooled to room temperature and then the organic layer was subjected to filtration treatment to remove a salt, and then the filtered organic layer was distilled. This was added again to 134 ml (10 times the amount) of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 5 (7.6 g, 57%, MS: [M+H]+=882.3).

Synthesis Example 6: Preparation of Compound 6

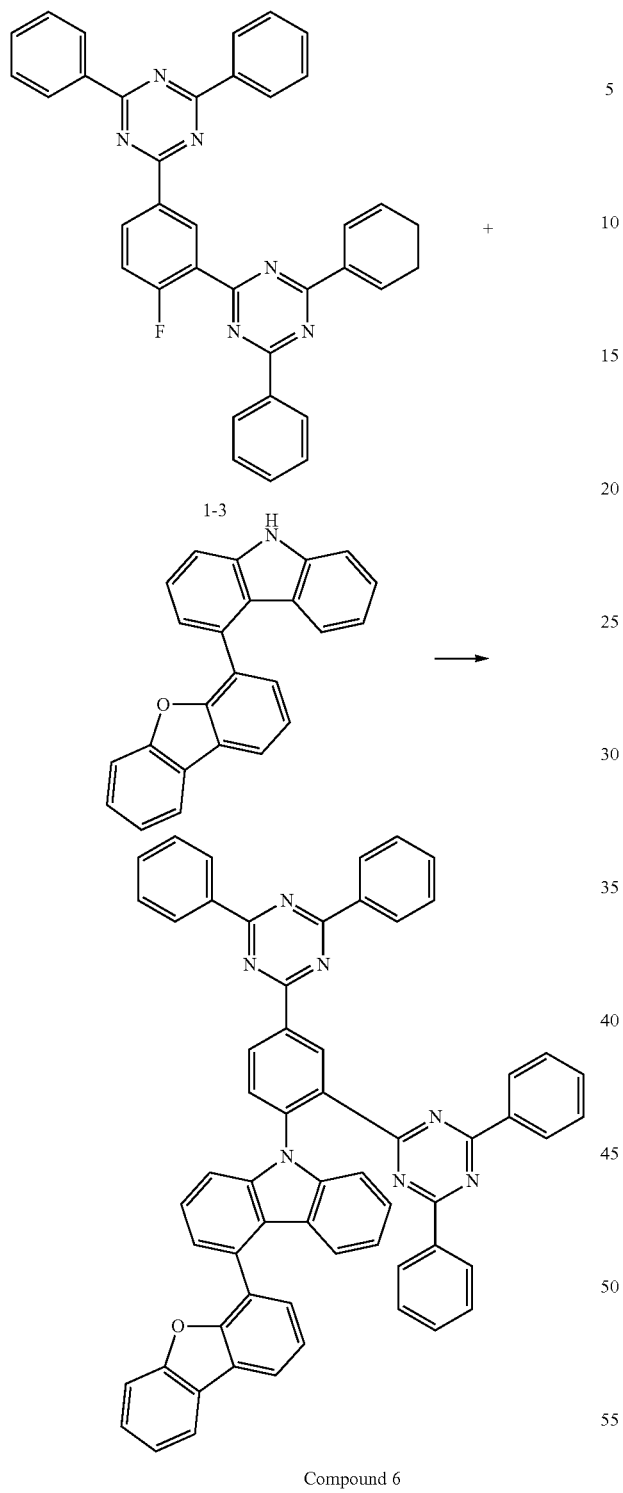

Compound 6

Compound 1-3 (10 g, 17.9 mmol) and 4-(dibenzo[b,d]furan-4-yl)-9H-carbazole (6 g, 17.9 mmol) were added to 200 ml of dimethylformamide under a nitrogen atmosphere, and the mixture was stirred and refluxed. Then, sodium tert-butoxide (11.4 g, 53.7 mmol) was added thereto and sufficiently stirred, and then bis(tri-tert-butylphosphine)palladium (0.3 g, 0.5 mmol) was added. After reacting for 6 hours, the reaction mixture was cooled to room temperature and then the organic layer was subjected to filtration treatment to remove a salt, and then the filtered organic layer was distilled. This was added again to 156 ml (10 times the amount) of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 6 (10 g, 64%, MS: [M+H]+=872.3).

Synthesis Example 7: Preparation of Compound 7

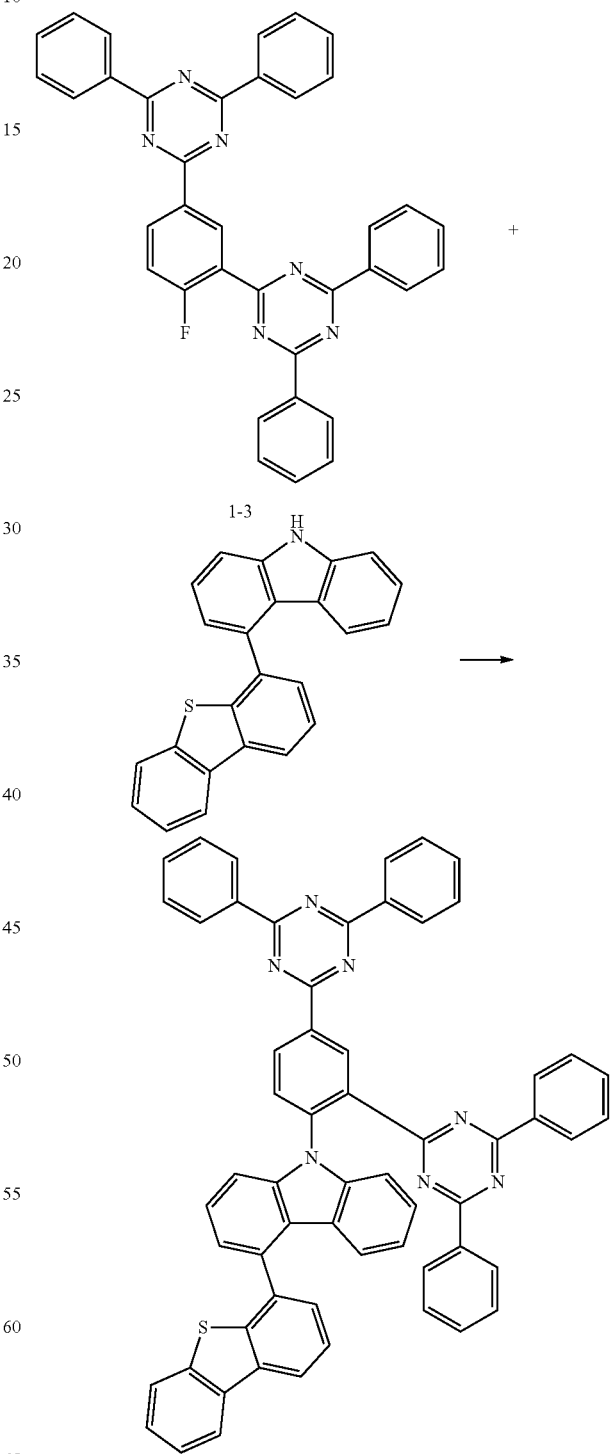

Compound 7

Compound 1-3 (10 g, 17.9 mmol) and 4-(dibenzo[b,d]thiophen-4-yl)-9H-carbazole (6.3 g, 17.9 mmol) were added to 200 ml of dimethylformamide under a nitrogen atmosphere, and the mixture was stirred and refluxed. Then, sodium tert-butoxide (11.4 g, 53.7 mmol) was added thereto and sufficiently stirred, and then bis(tri-tert-butylphosphine)palladium (0.3 g, 0.5 mmol) was added. After reacting for 4 hours, the reaction mixture was cooled to room temperature and then the organic layer was subjected to filtration treatment to remove a salt, and then the filtered organic layer was distilled. This was added again to 159 ml (10 times the amount) of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 7 (11.9 g, 75%, MS: [M+H]+=888.3).

Synthesis Example 8: Preparation of Compound 8

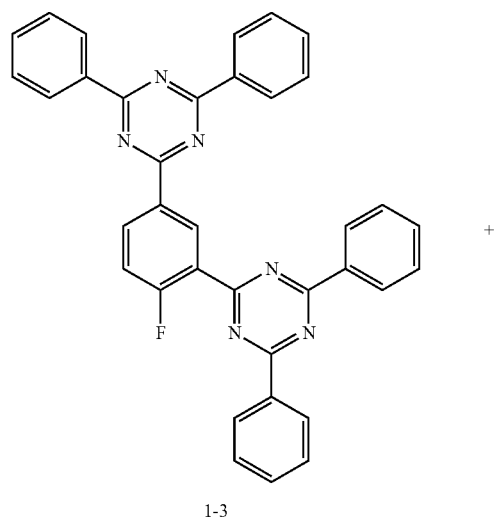

1-3

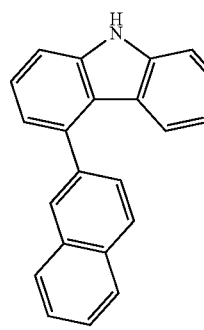

+

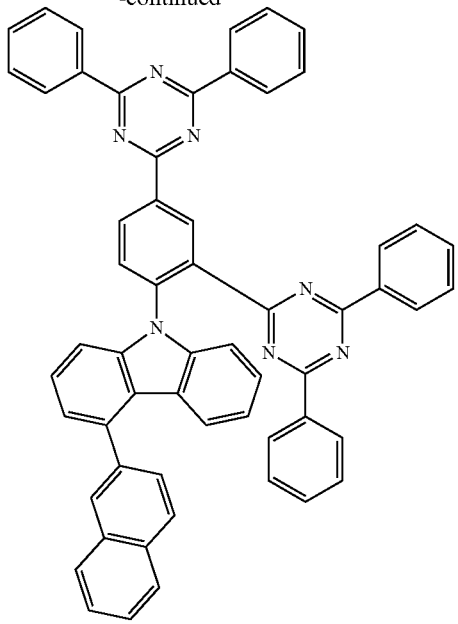

Compound 8

Compound 1-3 (10 g, 17.9 mmol) and 4-(naphthalen-2-yl)-9H-carbazole (5.3 g, 17.9 mmol) were added to 200 ml of dimethylformamide under a nitrogen atmosphere, and the mixture was stirred and refluxed. Then, sodium tert-butoxide (11.4 g, 53.7 mmol) was added thereto and sufficiently stirred, and then bis(tri-tert-butylphosphine)palladium (0.3 g, 0.5 mmol) was added. After reacting for 7 hours, the reaction mixture was cooled to room temperature and then the organic layer was subjected to filtration treatment to remove a salt, and then the filtered organic layer was distilled. This was added again to 149 ml (10 times the amount) of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound 8 (10.4 g, 70%, MS: [M+H]+=832.3).

Synthesis Example 9: Preparation of Comparative Compound 2

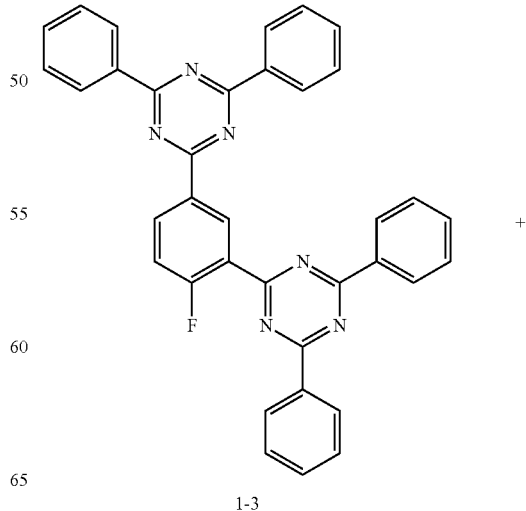

1-3

+

-continued

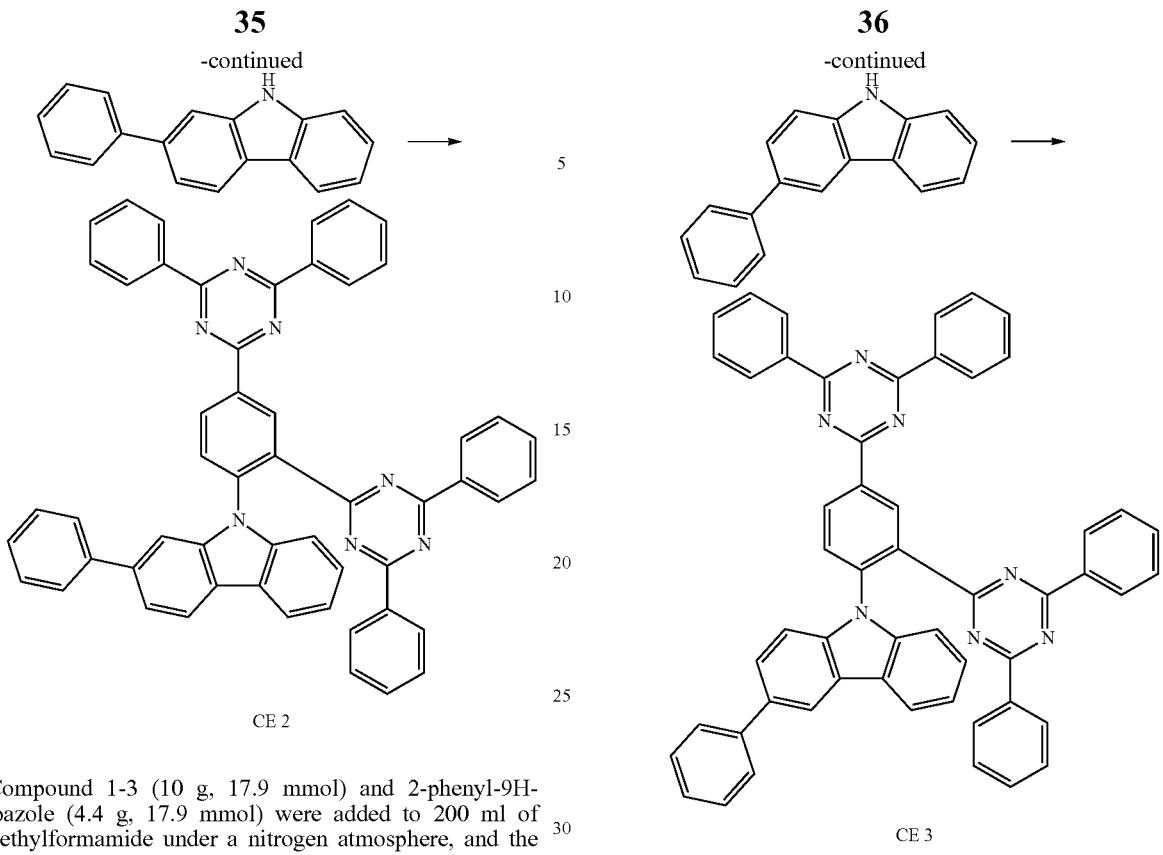

CE 2

Compound 1-3 (10 g, 17.9 mmol) and 2-phenyl-9H-carbazole (4.4 g, 17.9 mmol) were added to 200 ml of dimethylformamide under a nitrogen atmosphere, and the mixture was stirred and refluxed. Then, sodium tert-butoxide (11.4 g, 53.7 mmol) was added thereto and sufficiently stirred, and then bis(tri-tert-butylphosphine)palladium (0.3 g, 0.5 mmol) was added. After reacting for 3 hours, the reaction mixture was cooled to room temperature and then the produced solid was filtered. The solid was added to 420 ml (30 times the amount) of chloroform, dissolved and washed twice with water. The organic layer was then separated, anhydrous magnesium sulfate was added, stirred and then filtered. The filtrate was distilled under reduced pressure. The concentrated compound was purified by a silica column using chloroform and ethyl acetate to give a yellow solid compound CE 2 (8.4 g, 60%, MS: [M+H]+=782.3).

Synthesis Example 10: Preparation of Comparative Compound 3

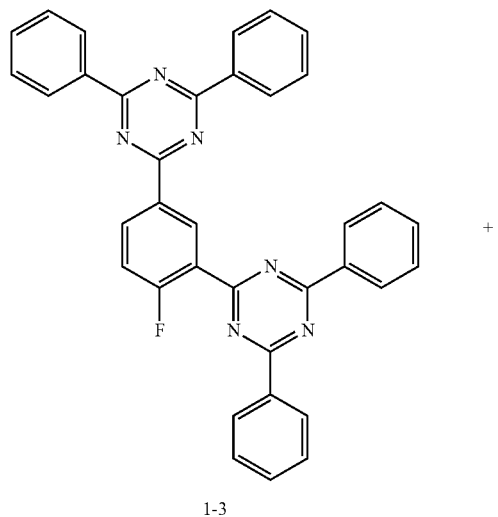

1-3

CE 3

Compound 1-3 (10 g, 17.9 mmol) and 3-phenyl-9H-carbazole (6.3 g, 17.9 mmol) were added to 200 ml of dimethylformamide under a nitrogen atmosphere, and the mixture was stirred and refluxed. Then, sodium tert-butoxide (11.4 g, 53.7 mmol) was added thereto and sufficiently stirred, and then bis(tri-tert-butylphosphine)palladium (0.3 g, 0.5 mmol) was added. After reacting for 6 hours, the reaction mixture was cooled to room temperature and then the produced solid was filtered. The solid was added to 420 ml (30 times the amount) of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethyl acetate to give a yellow solid compound CE 3 (7 g, 50%, MS: [M+H]+=782.3).

EXAMPLES

Experimental Example 1

A glass substrate on which ITO (indium tin oxide) was coated as a thin film to a thickness of 1,300 Å was put into distilled water in which a detergent was dissolved, and ultrasonically cleaned. A product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. The substrate was cleaned for 5 minutes using oxygen plasma and then transferred to a vacuum depositor.

On the ITO transparent electrode thus prepared, a compound HI-1 below was thermally vacuum-deposited to a thickness of 50 Å to form a hole injection layer. A compound HT-1 below was thermally vacuum-deposited to a thickness of 250 Å on the hole injection layer to form a hole transport layer, and a compound HT-2 below was vacuum-deposited to a thickness of 50 Å on the HT-1 deposited layer to form an electron blocking layer. Compound 1 prepared in the previous Synthesis Example 1, a compound YGH-1 below and a phosphorescent dopant YGD-1 below were co-deposited in a weight ratio of 44:44:12 on the HT-2 deposited layer to form a light emitting layer with a thickness of 400 Å. A compound ET-1 below was vacuum-deposited to a thickness of 250 Å on the light emitting layer to form an electron transport layer, and a compound ET-2 below and Li were vacuum-deposited in a weight ratio of 98:2 n the electron transport layer to form an electron injection layer with a thickness of 100 Å. Aluminum was deposited to a thickness of 1000 Å on the electron injection layer to form a cathode.

-continued

HT-2

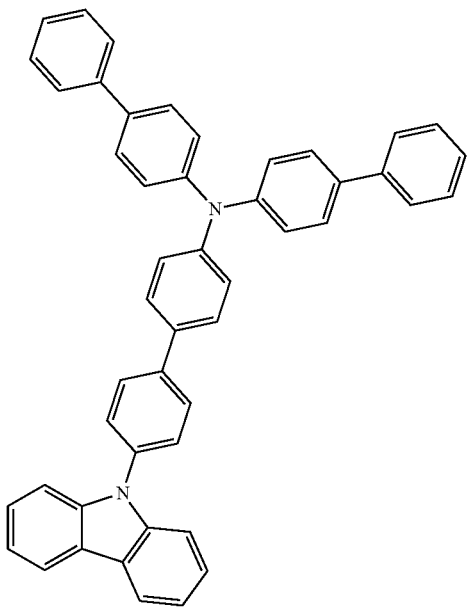

HI-1

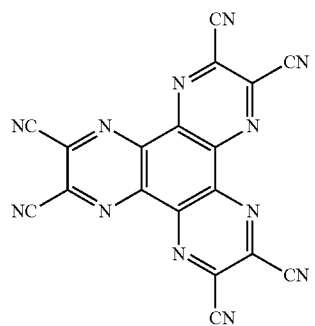

YGH-1

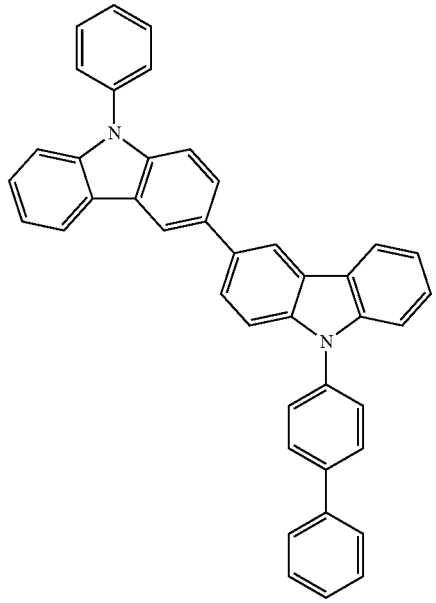

HT-1

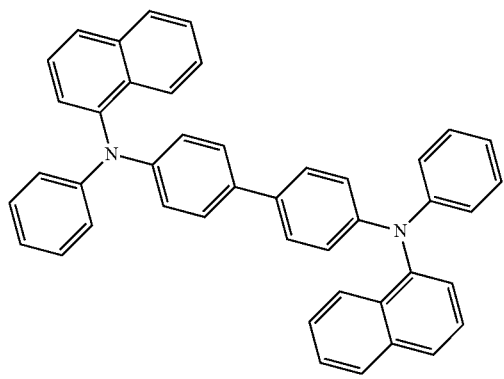

YGD-1

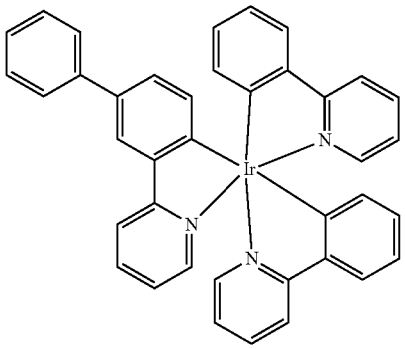

ET-1

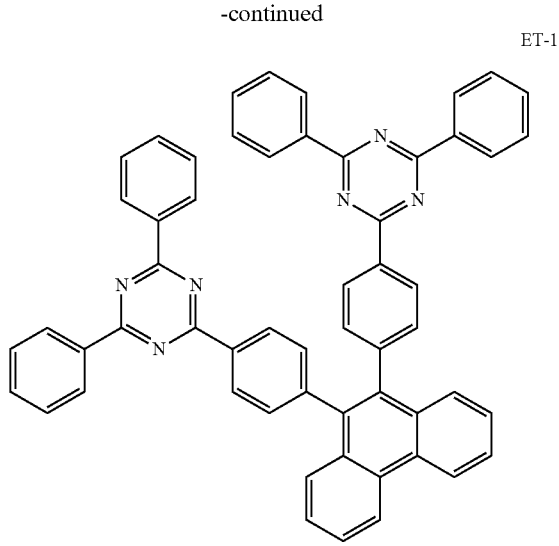

ET-2

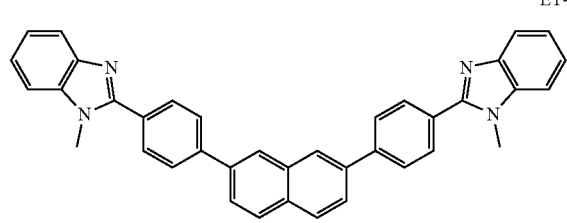

In the above-mentioned process, the vapor deposition rate of the organic material was maintained at 0.4 to 0.7 Å/sec, the deposition rate of aluminum was maintained at 2 Å/sec, and the degree of vacuum during the deposition was maintained at $1\times10^{-7}$ to $5\times10^{-8}$ torr.

Experimental Examples 2 to 8

The organic light emitting devices were manufactured in the same manner as in Experimental Example 1, except that the compounds shown in Table 1 below were used instead of Compound 1 of Synthesis Example 1 in Experimental Example 1.

Comparative Experimental Examples 1 to 3

The organic light emitting devices were manufactured in the same manner as in Experimental Example 1, except that the compounds shown in Table 1 below were used instead of Compound 1 of Synthesis Example 1 in Experimental Example 1. In Table 1, the compounds CE1 to CE3 are as follows.

CE1

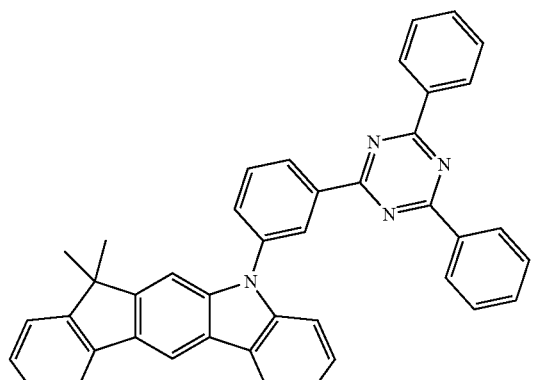

CE 2

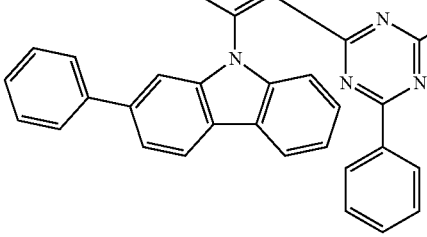

CE 3

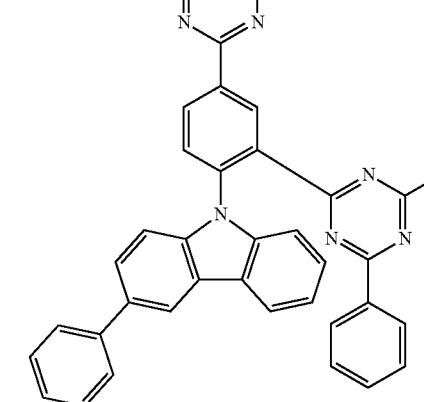

The voltage and efficiency of the organic light emitting devices manufactured in Experimental Examples and Comparative Experimental Examples were measured at a current density of 10 mA/cm², and the lifetime was measured at a current density of 50 mA/cm². The results are shown in Table 1 below. At this time, LT95 means the time required for the luminance to be reduced to 95% of the initial luminance.

TABLE 1

| | Compound | Voltage(V) (@10 mA/cm$^2$) | Efficiency (Cd/A) (@10 mA/cm$^2$) | Color coordinate (x, y) | Lifetime (h) (LT$_{95}$ at 50 mA/cm$^2$) |
|---|---|---|---|---|---|
| Exp Ex 1 | Compound 1 | 4.1 | 91 | 0.44, 0.51 | 195 |
| Exp Ex 2 | Compound 2 | 4.2 | 90 | 0.46, 0.53 | 183 |
| Exp Ex 3 | Compound 3 | 4.1 | 91 | 0.46, 0.54 | 197 |
| Exp Ex 4 | Compound 4 | 4.3 | 89 | 0.46, 0.54 | 165 |
| Exp Ex 5 | Compound 5 | 4.4 | 88 | 0.46, 0.53 | 177 |
| Exp Ex 6 | Compound 6 | 4.3 | 85 | 0.46, 0.53 | 164 |
| Exp Ex 7 | Compound 7 | 4.4 | 89 | 0.46, 0.54 | 145 |
| Exp Ex 8 | Compound 8 | 4.5 | 87 | 0.46, 0.54 | 140 |
| Comp Exp Ex 1 | CE1 | 4.7 | 70 | 0.46, 0.54 | 39 |
| Comp Exp Ex 2 | CE2 | 4.5 | 83 | 0.46, 0.55 | 115 |
| Comp Exp Ex 3 | CE3 | 4.5 | 83 | 0.46, 0.55 | 126 |

As shown in Table 1, when the compound of the present disclosure is used as a light emitting layer material, it was confirmed that it exhibits excellent efficiency and lifetime as compared with Comparative Experimental Examples. This is considered to be because the electron stability is increased through additional bonds between intramolecular orbitals.

In addition, when the bond is formed at position 4 of the substitution position of the carbazole substituent, it can be confirmed that the lifetime characteristics are most excellent. This is considered to be because the phenomenon of increasing the electronic stability as described above appears most highly in these structures.

EXPLANATION OF SYMBOLS

| | |
|---|---|
| 1: substrate | 2: anode |
| 3: light emitting layer | 4: cathode |
| 5: hole injection layer | 6: hole transport layer |
| 7: light emitting layer | 8: electron transport layer |
| 9: electron blocking layer | 10: electron injection layer |

The invention claimed is:

1. A compound of Chemical Formula 1:

Chemical Formula 1

[Structure showing Ar$_1$, Ar$_2$ connected via X$_1$ ring, linked to phenyl group bonded to carbazole (with Ar$_5$ and (R$_1$)$_n$) and to X$_2$ ring bearing Ar$_3$ and Ar$_4$]

wherein, in Chemical Formula 1:

each X$_1$ is independently N or CH, with the proviso that at least one of them is N;

each X$_2$ is independently N or CH, with the proviso that at least one of them is N;

Ar$_1$ to Ar$_4$ are each independently a substituted or unsubstituted C$_{6-60}$ aryl or a substituted or unsubstituted C$_{5-60}$ heteroaryl containing any one or more heteroatoms selected from the group consisting of N, O, and S;

Ar$_5$ is a substituted or unsubstituted C$_{6-60}$ aryl or a substituted or unsubstituted C$_{5-60}$ heteroaryl containing any one or more heteroatoms selected from the group consisting of N, O, and S;

each R$_1$ is independently hydrogen, deuterium, a substituted or unsubstituted C$_{1-60}$ alkyl, a substituted or unsubstituted C$_{3-60}$ cycloalkyl, a substituted or unsubstituted C$_{6-60}$ aryl, or a substituted or unsubstituted C$_{5-60}$ heteroaryl containing one or more heteroatoms selected from the group consisting of N, O, and S; and n is an integer of 0 to 4.

2. The compound of claim 1, wherein:

Ar$_1$ to Ar$_4$ are each independently a phenyl, biphenyl, or naphthyl.

3. The compound of claim 1, wherein all of Ar$_1$ to Ar$_4$ are phenyl.

4. The compound of claim 1, wherein:

Ar$_5$ is a phenyl, biphenyl, naphthyl, dibenzofuranyl, or dibenzothiophenyl.

5. The compound of claim 1, wherein Ar$_5$ is phenyl.

6. The compound of claim 1, wherein:

each X$_1$ is N.

7. The compound of claim 1, wherein:

each X$_2$ is N.

8. The compound of claim 1, wherein n is 0.

9. The compound of claim 1, wherein:

the compound of Chemical Formula 1 is any one compound selected from the group consisting of the following compounds:

-continued
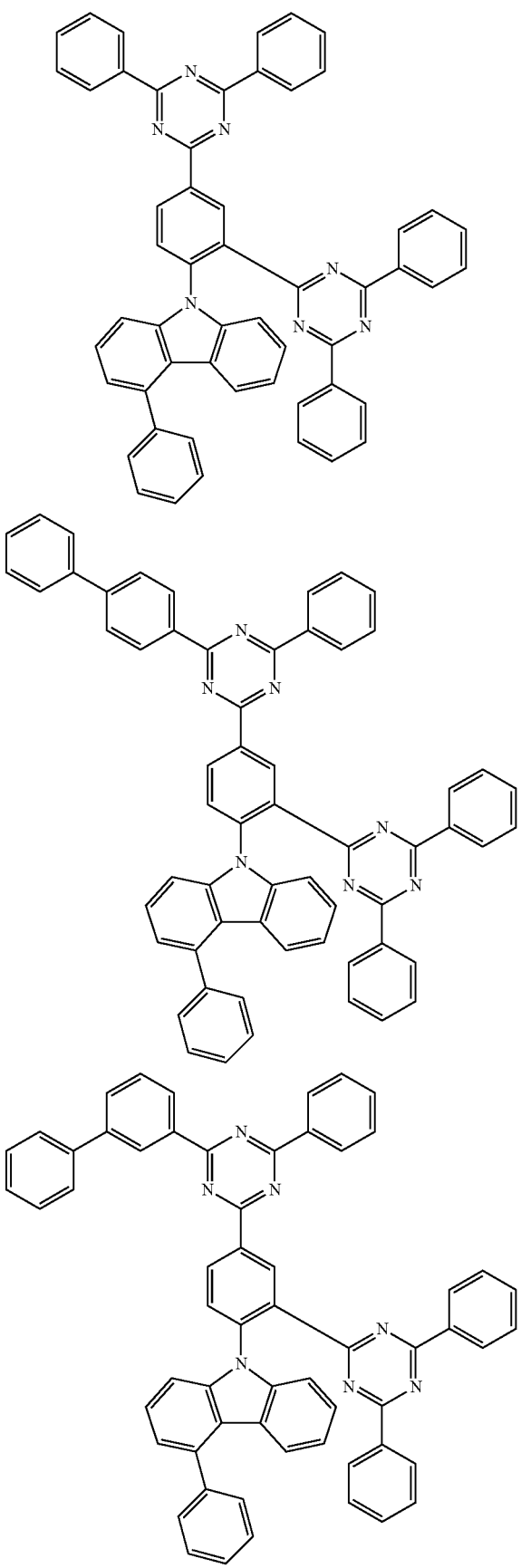
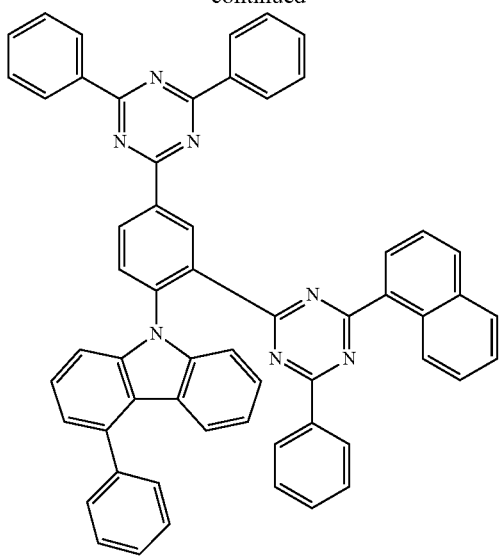
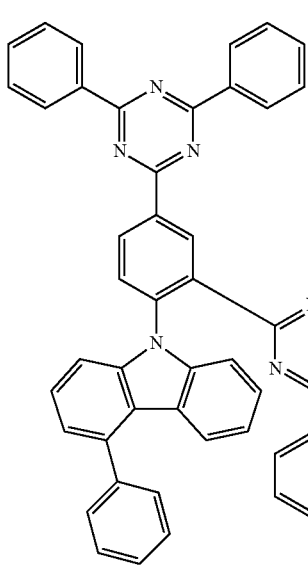
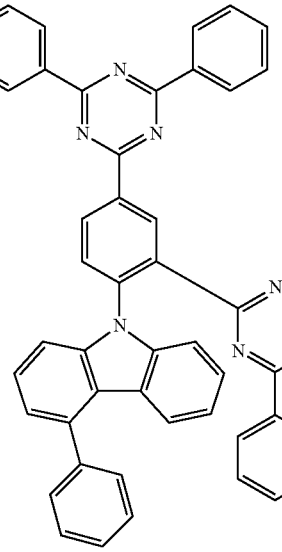

45
-continued

46
-continued

-continued
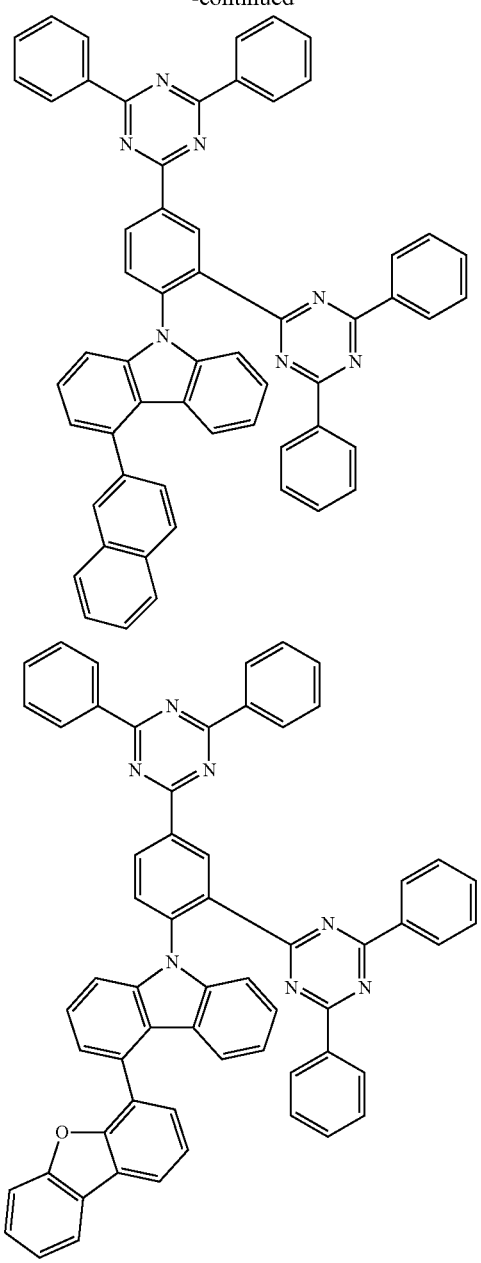
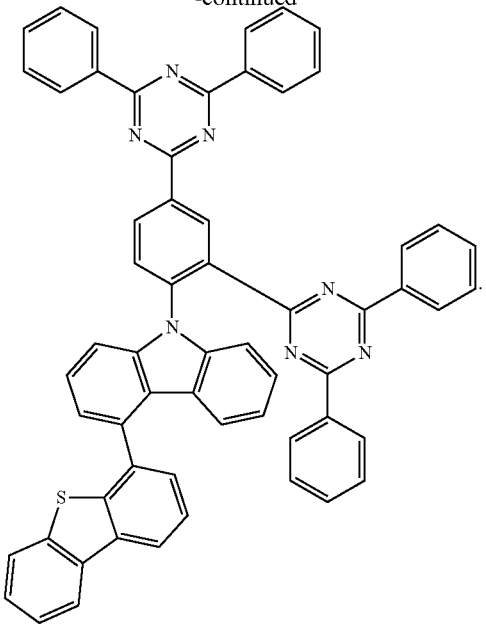
10. An organic light emitting device, comprising:
  a first electrode;
  a second electrode that is disposed opposite to the first electrode; and
  one or more organic material layers that are disposed between the first electrode and the second electrode, wherein one or more one layers of the organic material layers comprise the compound of claim 1.
* * * * *